United States Patent
McKinney et al.

(10) Patent No.: US 6,691,703 B2
(45) Date of Patent: Feb. 17, 2004

(54) CPR BARRIER DEVICE

(75) Inventors: Larry T. McKinney, Yorktown Heights, NY (US); James R. Traut, Poughkeepsie, NY (US); John G. Cline, LaGrangeville, NY (US); Sean Landis Phillips, New Paltz, NY (US); Andrew Serbinski, Annandale, NJ (US); Mirzat Koc, Brooklyn, NY (US); Mark Rosen, Hackensack, NJ (US)

(73) Assignee: Laerdal Medical Corporation, Wappinger Falls, NY (US)

( * ) Notice: Subject to any disclaimer, the term of this patent is extended or adjusted under 35 U.S.C. 154(b) by 66 days.

(21) Appl. No.: 09/773,325

(22) Filed: Jan. 31, 2001

(65) Prior Publication Data

US 2002/0100475 A1 Aug. 1, 2002

(51) Int. Cl.[7] .............................................. A61M 16/00
(52) U.S. Cl. .............................. 128/203.11; 128/202.28; 128/202.29
(58) Field of Search ..................... 128/202.28, 202.29, 128/203.11, 205.24, 206.21, 206.26, 206.28, 207.12, 205.25, 206.24; D24/110.4, 110.5; 2/9, 206, 244, 248

(56) References Cited

U.S. PATENT DOCUMENTS

| | | | |
|---|---|---|---|
| 1,653,572 A | * 12/1927 | Jackson | 128/206.24 |
| RE24,193 E | * 8/1956 | Emerson | 128/29 |
| 3,357,426 A | * 12/1967 | Cohen | 128/206.24 |
| 3,626,936 A | 12/1971 | Barker | |
| 3,695,264 A | 10/1972 | Laeral | |
| 4,510,931 A | 4/1985 | Henderson et al. | |
| 4,711,237 A | 12/1987 | Kaiser | |
| 4,811,730 A | 3/1989 | Milano | |
| 4,819,628 A | 4/1989 | Eisenberg et al. | |
| 4,834,085 A | 5/1989 | Webster, II | |
| 4,858,605 A | 8/1989 | Levy | |
| 4,909,245 A | 3/1990 | Wollenhaupt | |
| 5,088,485 A | 2/1992 | Schock | |
| 5,095,898 A | 3/1992 | Don Michael | |
| 5,119,809 A | 6/1992 | Gerson | |
| 5,121,745 A | 6/1992 | Israel | |
| 5,127,397 A | 7/1992 | Kohnke | |
| 5,146,914 A | * 9/1992 | Sturrock | 128/203.11 |
| 5,161,523 A | 11/1992 | Gilbert | |
| 5,165,396 A | 11/1992 | Don Michael et al. | |
| 5,176,658 A | 1/1993 | Ranford | |
| 5,295,478 A | * 3/1994 | Baldwin | 128/203.11 |
| 5,355,877 A | 10/1994 | Cheng | |
| 5,429,683 A | * 7/1995 | LeMitouard | 128/206.24 |
| 5,437,269 A | 8/1995 | Gooch | |
| 5,465,712 A | * 11/1995 | Malis et al. | 128/205.25 |
| 5,469,842 A | * 11/1995 | Flynn | 128/203.11 |
| 5,476,092 A | * 12/1995 | Karlis et al. | 128/203.11 |
| 5,501,214 A | 3/1996 | Sabo | |
| 5,511,543 A | 4/1996 | Shirley | |
| 5,562,093 A | * 10/1996 | Gerson | 128/203.11 |
| 5,575,279 A | 11/1996 | Beplate | |
| 5,584,288 A | 12/1996 | Baldwin | |

(List continued on next page.)

*Primary Examiner*—Weilun Lo
*Assistant Examiner*—Teena Mitchell
(74) *Attorney, Agent, or Firm*—Frommer Lawrence & Haug LLP; William F. Lawrence; Matthew K. Ryan

(57) ABSTRACT

A resuscitation device for providing a barrier between a rescuer and a patient requiring mouth-to-mouth resuscitation. This resuscitation device includes an inflatable portion which when inflated extends in the breathing direction between the rescuer and the patient so as to be placed around at least one breathing organ of the victim. An inflation member receives airflow from the rescuer to inflate the inflatable portion. In this resuscitation device, a valve assembly permits airflow from the rescuer to the patient and diverts the exhalation and body fluids of the patient from reaching the rescuer. An additional barrier member can also be provided for shielding the rescuer from the patient.

96 Claims, 39 Drawing Sheets

U.S. PATENT DOCUMENTS

| | | | |
|---|---|---|---|
| 5,664,559 A | | 9/1997 | Baldwin |
| 5,735,265 A | * | 4/1998 | Flynn .................... 128/203.11 |
| 5,765,551 A | | 6/1998 | Sugino |
| 5,787,880 A | * | 8/1998 | Swanson et al. ....... 128/202.28 |
| 5,813,423 A | | 9/1998 | Kirchgeorg |
| 5,829,433 A | | 11/1998 | Shigematsu et al. |
| D420,128 S | * | 2/2000 | Hoenig ................... D24/110.1 |
| 6,035,852 A | * | 3/2000 | Hoftman ................ 128/206.26 |
| 6,070,574 A | * | 6/2000 | O'Day et al. .......... 128/203.11 |

* cited by examiner

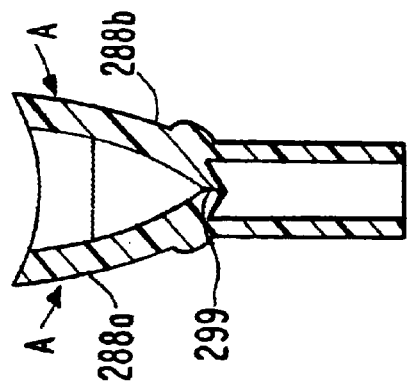
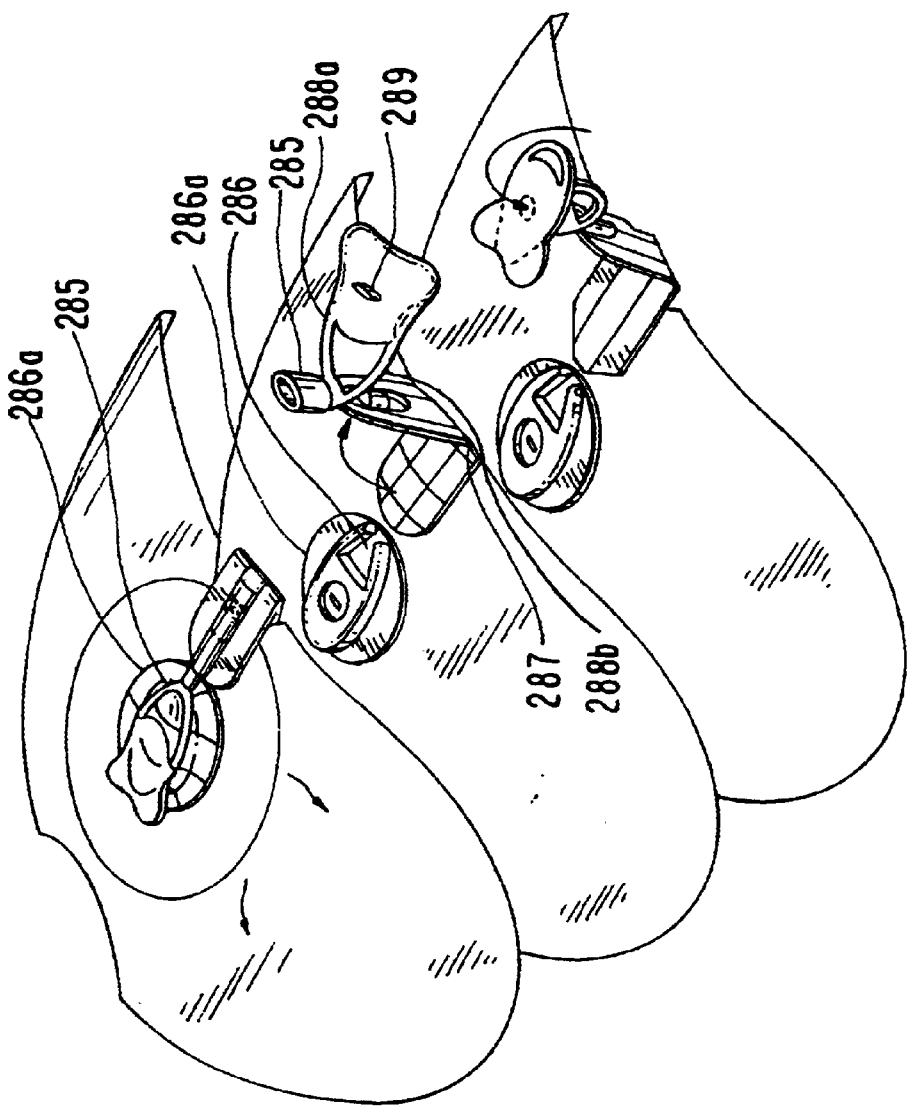
FIG.9b
FIG.9a

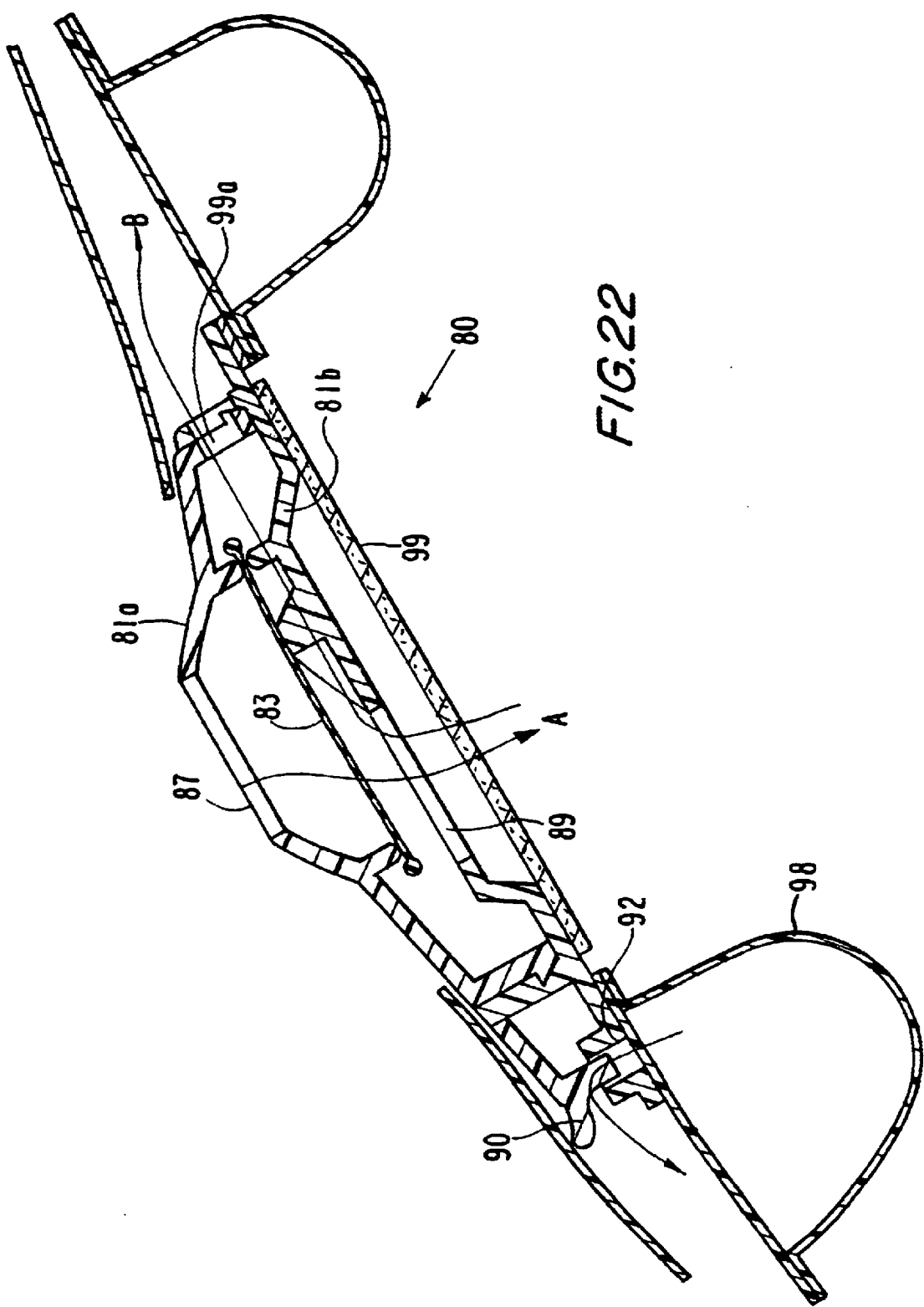

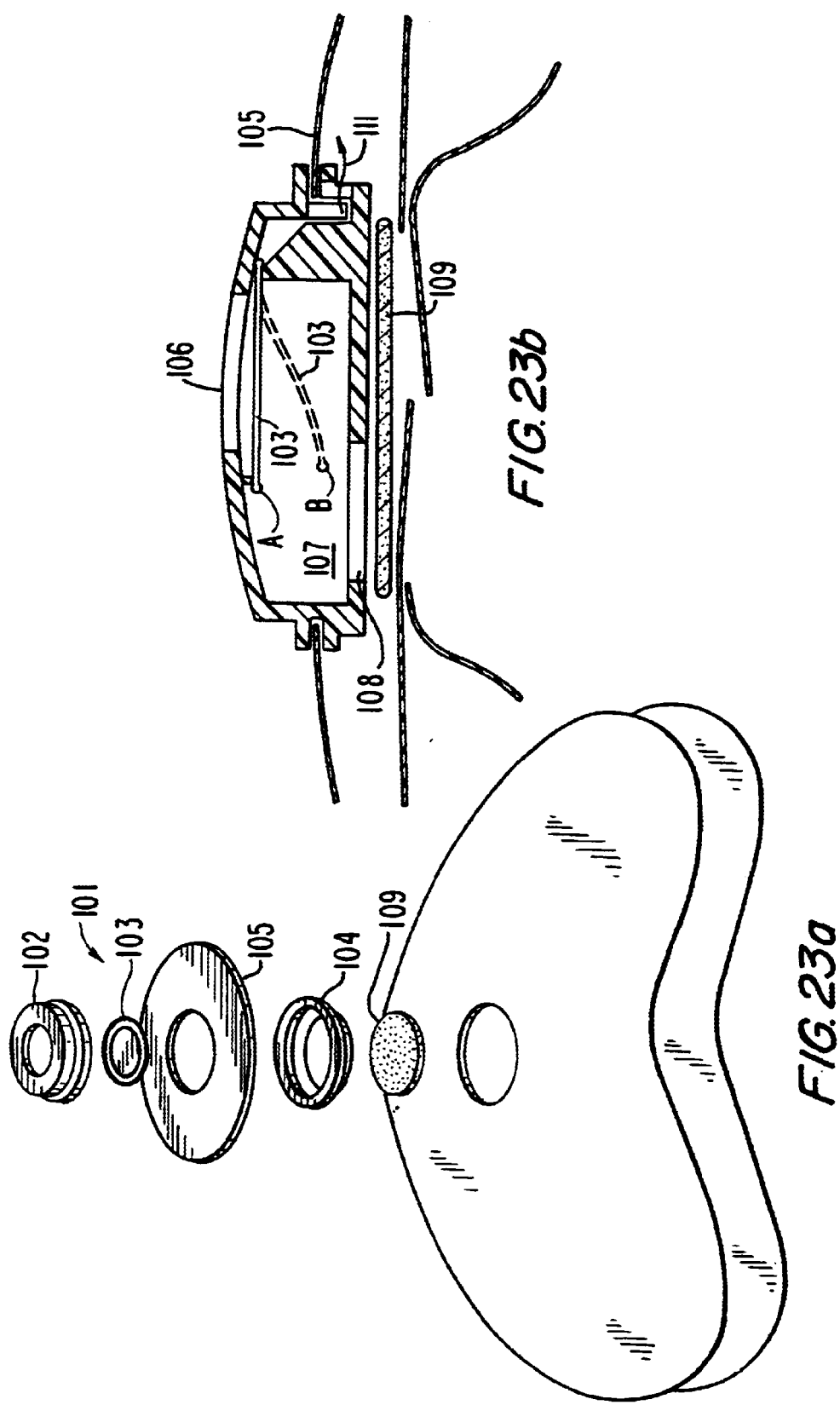

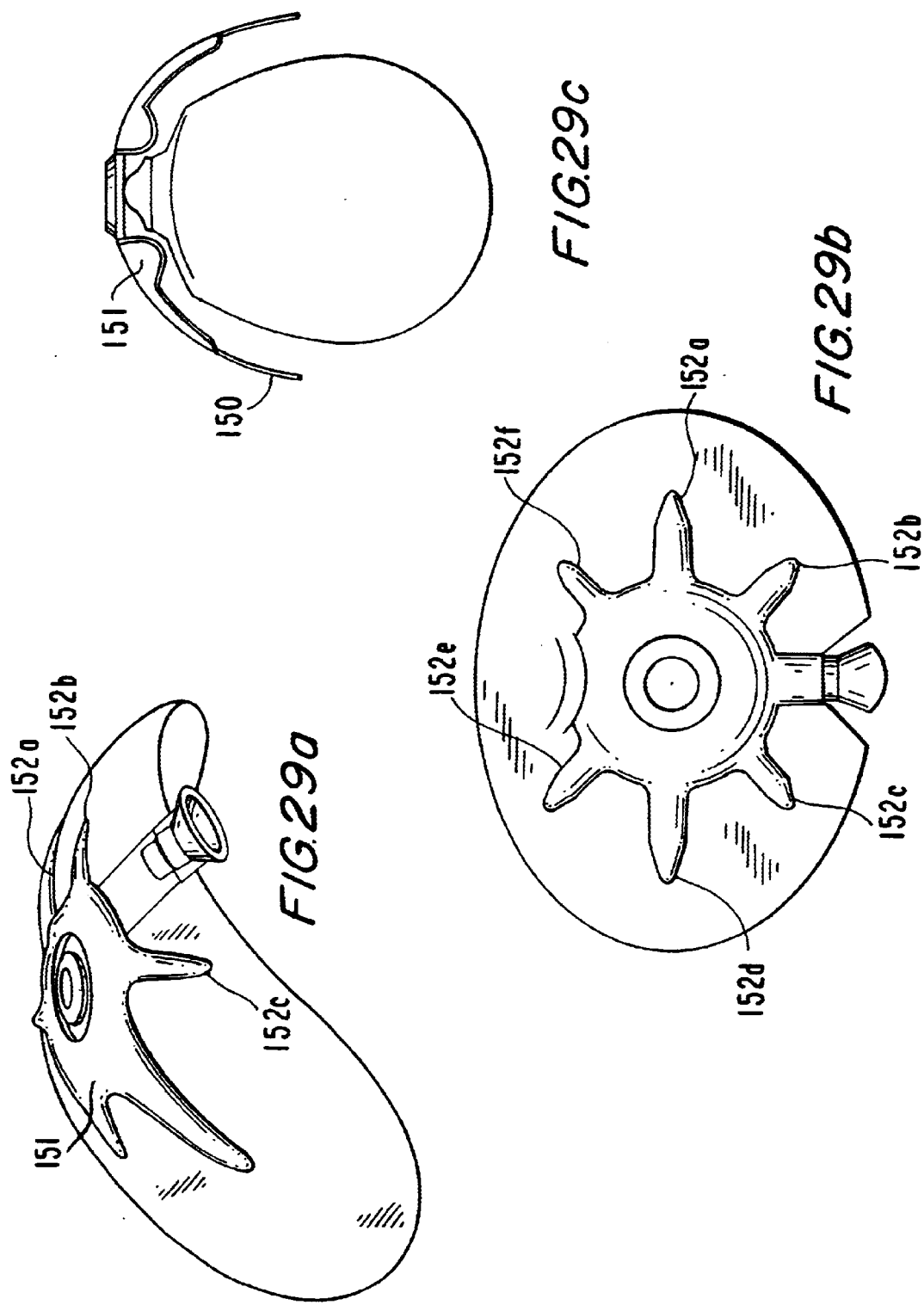

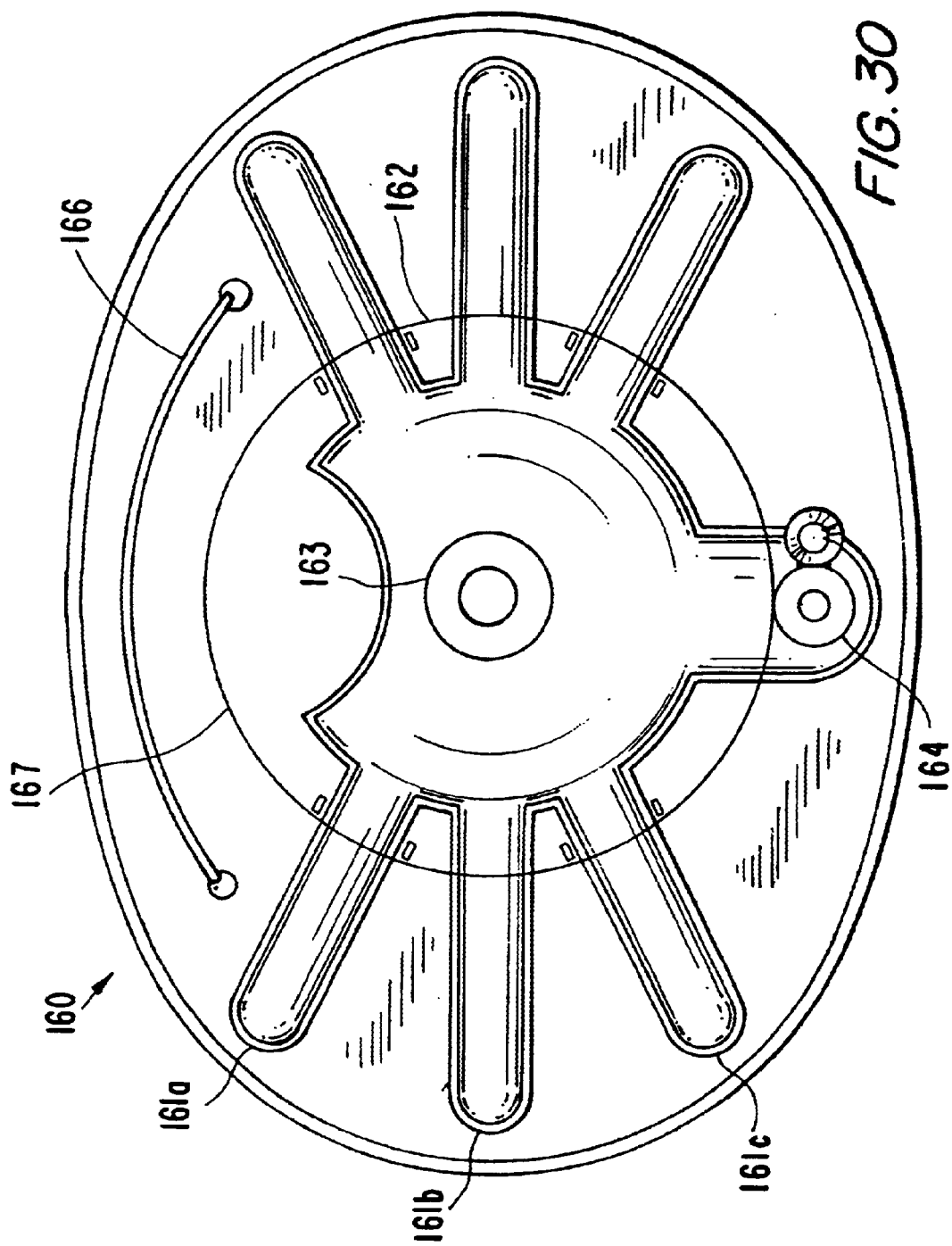

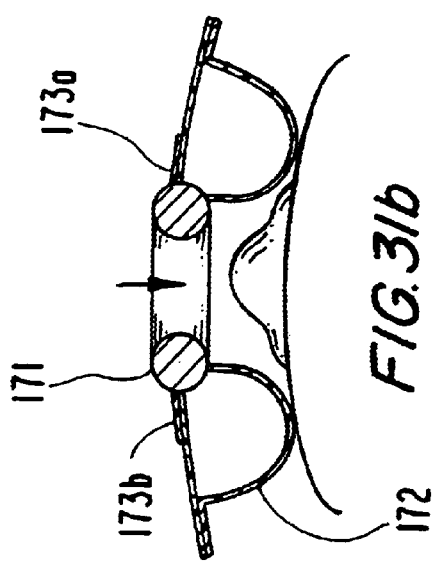
FIG.3/b
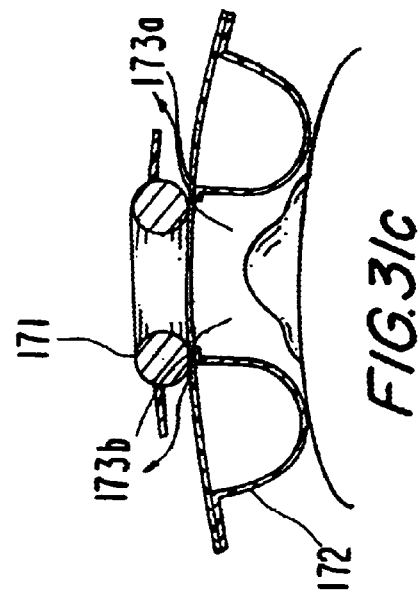
FIG.3/c
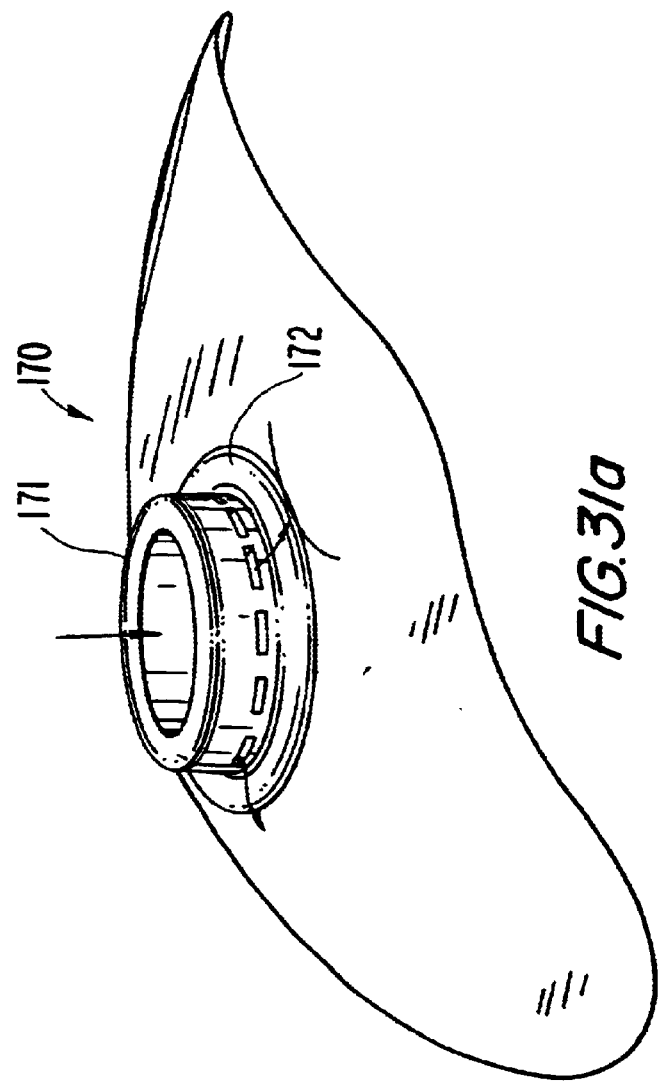
FIG.3/a ature and carry. It is further

CPR BARRIER DEVICE

FIELD OF THE INVENTION

This invention relates to the field of airway management devices, and more particularly, relates to a barrier device to be placed between the rescuer and the patient so as to protect the rescuer during administration of cardiopulmonary resuscitation ("CPR").

BACKGROUND OF THE INVENTION

A CPR barrier device is used to protect a rescuer administering CPR on a patient who has stopped breathing, has an obstructed airway, or is in cardiac arrest. It is intended to prevent direct facial contact with a victim and reduce the chance that the patient's exhalation or body fluids may enter the rescuer's mouth. It is thus intended that such devices reduce the risk of disease transmission and help overcome the reluctance of a rescuer to perform CPR.

Barrier devices can be placed into three categories based on features and price. These include (1) face shields with filters, (2) shields with one-way valves, and (3) masks with valves and filters. Shields are single use, smaller and more portable than masks. Masks may be single use or reusable and may include disposable valves and filters. In addition, by providing a better face seal, masks may be more effective at ventilation.

Obstacles to real life performance of CPR include lack of training, poor learning retention, and fear of disease. It is therefore desirable to provide a CPR barrier device which improves CPR performance, increases the perceived protection or separation of the rescuer from the patient, and makes the device more desirable to obtain and carry. It is further desirable to provide a CPR barrier device which improves the face seal and support training in use of the device.

Further, during CPR, it is sometimes necessary to close the nose air path of the patient. Typically, the nose is pinched by one hand of the rescuer. During administration of CPR, it has been found that an inexperienced rescuer is reluctant to pinch the nose with the required amount of pressure or does not apply pressure at all. Therefore, it has been also found desirable to provide a CPR barrier device which includes a nose pinch element which assists the rescuer in sealing the nose of the patient and to assist in properly orienting the CPR barrier device on the patient. It has further been found desirable to provide a nose pinch element for a CPR barrier device which only provides for indirect squeezing of the nose.

In order to provide better performance than current midrange barrier devices, it is further desirable to provide the barrier device with some type of one-way valve and air filter which incorporates patient exhalation diversion. It is also desirable to provide a CPR barrier device with improved volume delivery compared to current face shields.

Moreover, during CPR, time is of the essence. Many CPR barrier devices in use have been found difficult to deploy and properly orient on the face of the patient. It has therefore been found desirable to provide a CPR barrier device which can be rapidly and easily deployed by the rescuer and easily oriented on the face of the patient.

Another drawback of current CPR barrier devices for the general population is the lack of an incentive for the CPR barrier device to be carried by an individual on a regular basis. Therefore, it has been found extremely desirable to design carrying cases for a CPR barrier device which will motivate an individual to carry the CPR barrier device at all times.

OBJECTS OF THE INVENTION

It is therefore an object of this invention to provide a CPR barrier device which avoids the aforementioned deficiencies of the prior art.

It is also an object of this invention to provide a CPR barrier device wherein airflow is communicated in the direction of rescuer to patient, and the patient's exhalation is diverted from the rescuer.

It is another object of this invention to provide a CPR barrier device which prevents direct facial contact with a victim and reduces the chance that the patient's exhalation or body fluids enter the rescuer's mouth.

It is a further object of this invention to provide a CPR barrier device which includes a nose pinch element which assists the rescuer in sealing the nose of the patient.

It is yet another object of this invention to provide a CPR barrier device which includes a nose pinch element which provides for only indirect squeezing of the nose of the patient.

It is yet another object of this invention to provide a CPR barrier device which is of relatively low cost and disposable.

It is yet also an object of this invention to provide a CPR barrier device which can be rapidly and easily deployed by the rescuer.

It is yet a further object of this invention to provide a CPR barrier device which can be packaged in a variety of small carrying cases.

It is still another object of the present invention to provide a CPR barrier device which is easily oriented on the face of the patient.

Various other objects, advantages and features of the present invention will become readily apparent from the ensuing detailed description and the novel features will be particularly pointed out in the appended claims.

SUMMARY OF THE INVENTION

This invention relates to a resuscitation device for providing a barrier between a rescuer and a patient requiring mouth-to-mouth resuscitation. This resuscitation device includes an inflatable portion which when inflated extends in the breathing direction between the rescuer and the patient so as to be placed around at least one breathing organ of the patient; an inflation member which receives airflow from the rescuer to inflate the inflatable portion; and a ventilation/exhalation valve member for permitting airflow from the rescuer to the patient and for preventing exhalation and bodily fluids from reaching the rescuer.

In this resuscitation device, the inflatable portion can be formed of two sheets of flexible film to form an air chamber therebetween. The air chamber when inflated forms a pillow-like member to be placed around the breathing organ of the patient. This inflatable portion is inflatable between an uninflated condition, wherein the inflatable portion is capable of lying generally flat on the face of the patient on the breathing organ of the patient, and an inflated condition, wherein the inflatable portion is inflated in the breathing direction between the rescuer and the patient so as to be placed on the breathing organ of the patient. As a result, the resuscitation device of this invention permits mouth-to-mouth resuscitation to occur in both the uninflated and inflated conditions of the inflatable portion as time permits.

The inflation member of the CPR barrier device extends generally perpendicular to the breathing direction of the rescuer and includes an inflation valve member. This inflation valve member includes a blow tube which receives air from the rescuer to inflate the inflatable portion. The inflation valve member also includes a valve closing assembly which prevents air from escaping from the air chamber when the air chamber is sufficiently inflated. This valve closing assembly includes a pair of flexible flap members which open the valve air passage to the air chamber to admit air from the rescuer but close the valve air passage when sufficient back pressure is obtained within the air chamber.

In order to assist the rescuer in sealing the nose of the patient, the inflatable portion of the CPR barrier device of this invention may further include nose pinch elements. When the inflatable portion is inflated, the inflated nose pinch elements are pinched inwardly adjacent to the nostrils of the patient so as to be in a position to assist the rescuer in closing the nasal air passages. In addition, the nose pinch elements are designed so as to only provide an indirect squeezing force on the nose of the patient. When inflated, the nose pinch elements allow the inflatable portion to exhibit a three dimensional shape which conforms the CPR barrier device to the contour of the patient's face. Thus, the nose pinch elements further assist the rescuer in properly orienting the CPR barrier device on the face of the patient.

The ventilation/exhalation valve member is in the form of a one-way valve which has a flexible valve member for allowing air to flow from the rescuer to the patient but prevents the exhalation and bodily fluids of the patient from reaching the rescuer. In one preferred embodiment, this flexible valve member is a flexible diaphragm which is movable between a flexed condition, wherein ventilation from the rescuer to the patient is permitted, and an unflexed condition, wherein exhalation and bodily fluids of the patient are blocked from reaching the rescuer. The ventilation/exhalation valve member further includes an exhalation diversion opening formed therein through which the exhalation and bodily fluids of the patient are diverted when the exhalation and bodily fluids of the patient are blocked by the flexible diaphragm when the flexible diaphragm is in its unflexed condition. A covering member surrounds the exhalation diversion opening to shield the diverted patient exhalation from the rescuer. In addition, a filter may be contained within the ventilation/exhalation valve member which always filters the exhalation or bodily fluids of the patient.

In order to shield the rescuer from the patient, a barrier member may also be incorporated in this CPR barrier device. This barrier member is in the form of a flange member that surrounds the inflatable portion of the CPR barrier device. This barrier member not only provides a shield for the rescuer from exhalation and bodily fluids of the patient but also assists the rescuer by providing a hand gripping area to assist in placement of the CPR barrier device on the patient.

Additionally, the shape and size of the CPR barrier device of the present invention has been optimized so as to be as small as possible when it is in its folded, undeployed condition. Advantageously, in its folded, undeployed condition, the inflation member is presented (exposed) to the rescuer when the barrier device is removed from is packaging to reduce the time needed to deploy the CPR barrier device and inflate the inflatable portion thereof.

Thus, in accordance with the general objects of the present invention, the CPR barrier device of the present invention improves CPR performance and reduces the chance that the patient's exhalation or body fluids may contaminate the rescuer during CPR administration.

BRIEF DESCRIPTION OF THE DRAWINGS

The following detailed description given by way of example, but not intended to limit the invention solely to the specific embodiments described, may best be understood in conjunction with the accompanying drawings in which:

FIG. 3b is a side cross-sectional view of the CPR barrier device of FIG. 3a taken along line 3b—3b of FIG. 3a.

FIGS. 9a and 9b are various views explaining the operation of yet another inflation valve member which can be used in conjunction with the CPR barrier device of the present invention.

FIG. 22 is a side plan view of the valve assembly of FIG. 18 specifically illustrating the path of rescuer ventilation and patient exhalation and the addition of a hood assembly.

FIG. 23a is a front exploded perspective view of another preferred embodiment of a ventilation/exhalation valve assembly which can be incorporated in the CPR barrier device of the present invention.

FIG. 23b is a side sectional view of the valve assembly of FIG. 23a.

FIG. 29a is a top perspective view of another preferred embodiment of a CPR barrier device in accordance with the teachings of the present invention.

FIG. 29b is a top view of the CPR barrier device of FIG. 29a.

FIG. 29c illustrates positioning of the CPR barrier device of FIGS. 29a and 29b on the face of the patient.

FIG. 30 is a top plan view of another preferred embodiment of a CPR barrier device in accordance with the teachings of the present invention.

FIG. 31a is a front perspective view of another preferred embodiment of a CPR barrier device in accordance with the teachings of the present invention.

FIGS. 31b and 31c are front elevational views of the CPR barrier device of FIG. 31a in use.

FIG. 39b is a side cross-sectional view of the technique for inflating the inflatable portion through the patient valve assembly of FIG. 39a.

DETAILED DESCRIPTION OF CERTAIN PREFERRED EMBODIMENTS

Figure 1:
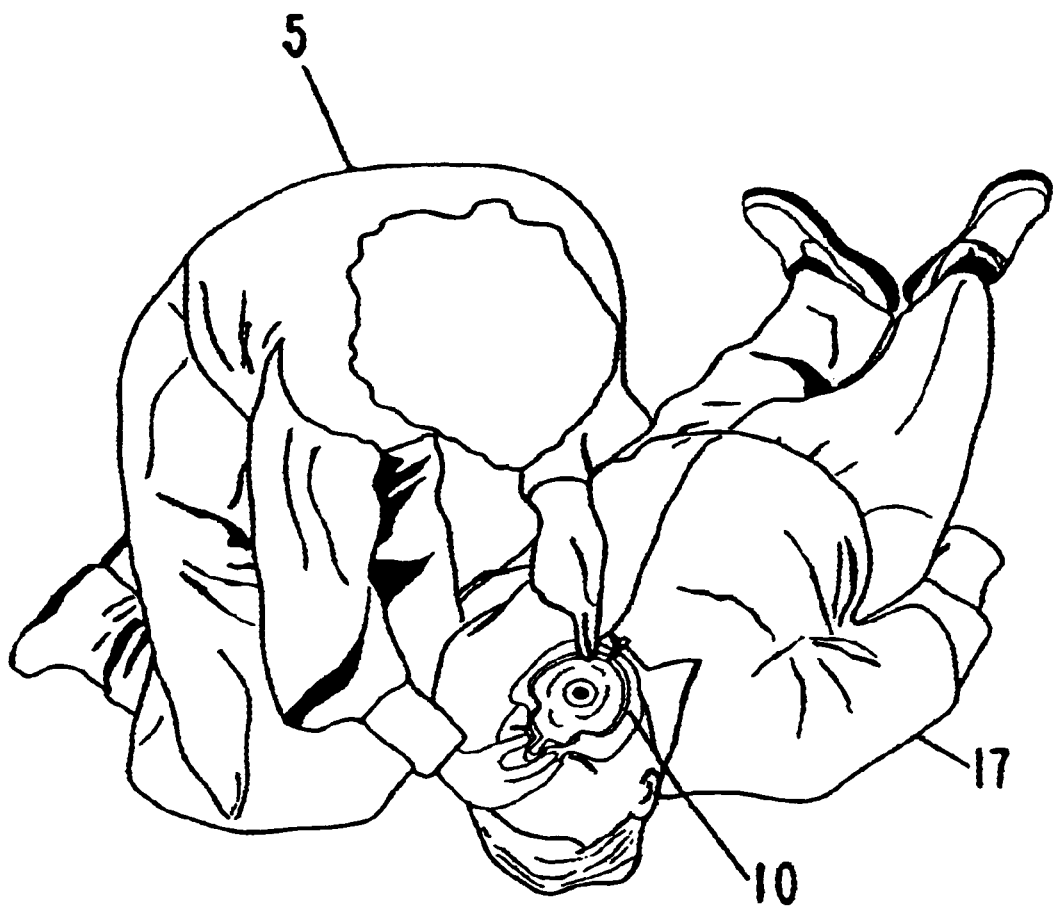
FIG. 1 is an illustration showing the CPR barrier device of the present invention in use.

Referring now to FIGS. 1, 2, 3a–b and 4 of the drawings, wherein like reference numerals represent like features in the several views, a resuscitation device 10 for providing a barrier between a rescuer 5 and a patient 7 requiring mouth-to-mouth resuscitation is provided. This resuscitation device is utilized in conjunction with cardiopulmonary resuscitation ("CPR"), and accordingly, this resuscitation device will hereinafter be referred to as a CPR barrier device.

Figure 2:
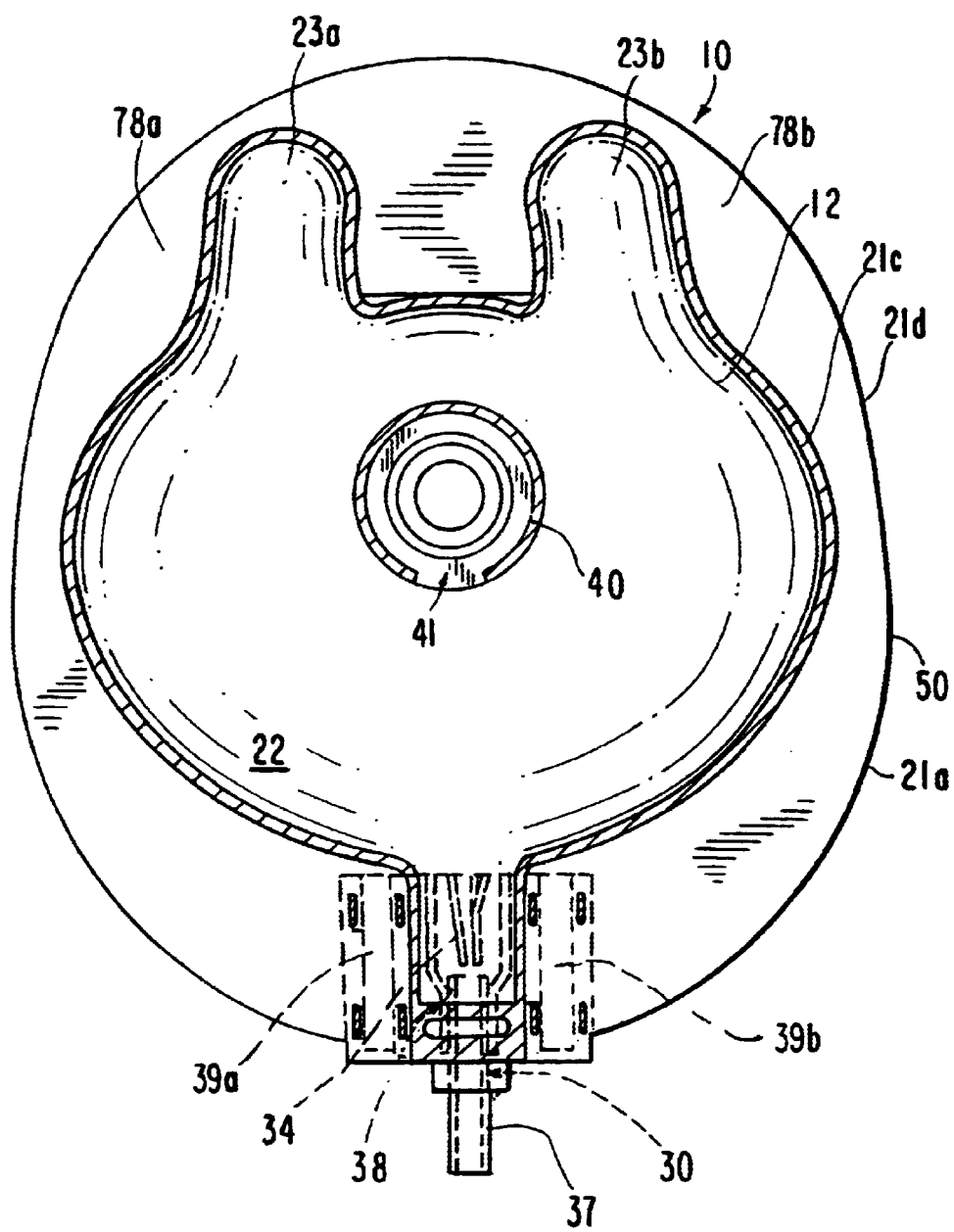
FIG. 2 is a top view of a preferred embodiment of a CPR barrier device in accordance with the teachings of the present invention with its inflatable portion in a deflated condition.
Figure 3A:
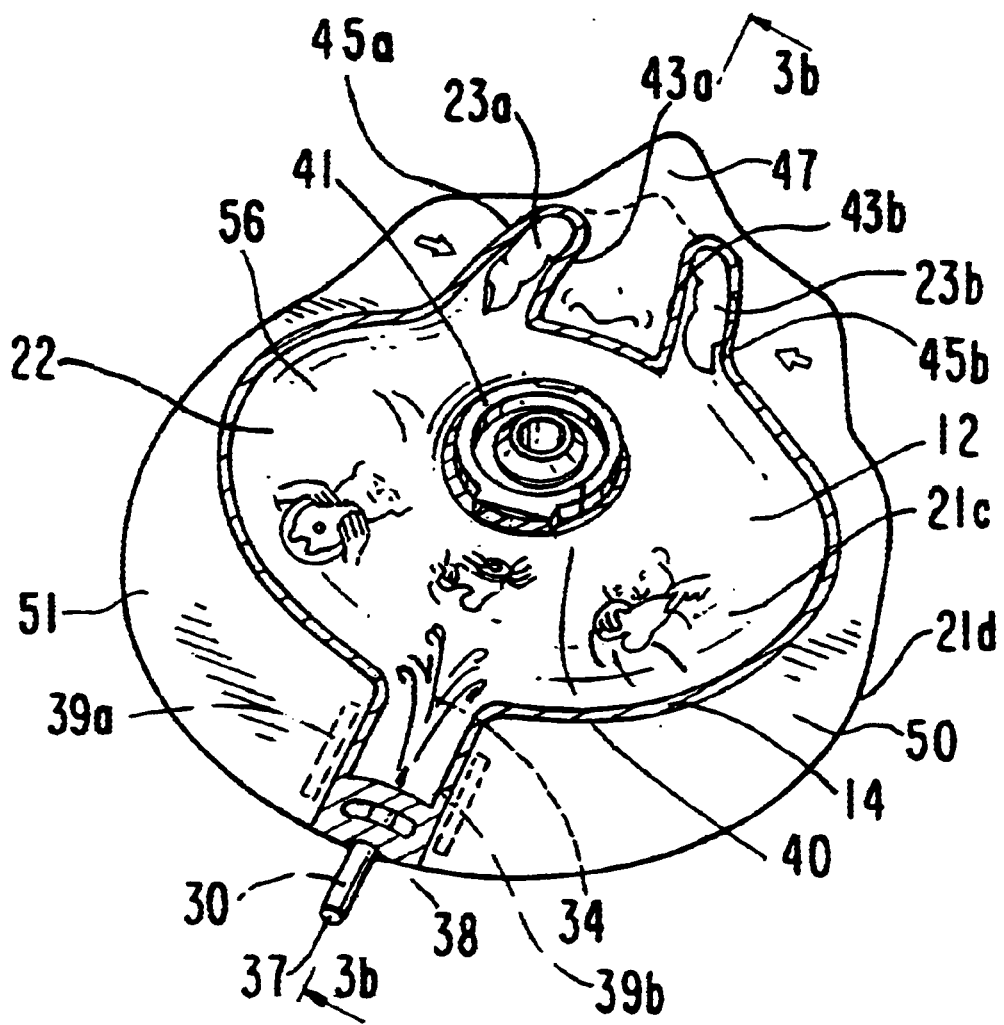
FIG. 3a is a top perspective view of the CPR barrier device of FIG. 2 with its inflatable portion in an inflated condition.
Figure 11:
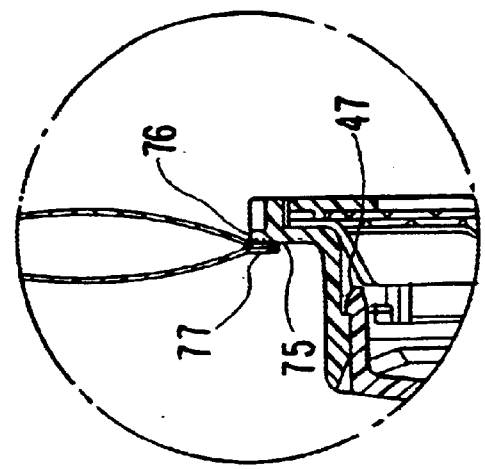
FIG. 11 is an exploded side cross-sectional view of a preferred embodiment of a ventilation/exhalation valve assembly for the CPR barrier device of the present invention.

As will be discussed in more detail below, this CPR barrier device is deployed by pulling it out of packaging and unfolding it. The unfolded, uninflated condition of the CPR barrier device 10 is shown in FIG. 2. As shown in FIG. 3a, an inflatable portion or pillow 12 is inflated and placed over the patient's mouth in the orientation indicated by the printing 14 on the rescuer's side of the device. Following CPR protocol, the rescuer exhales air through a ventilation/exhalation valve assembly 40 into the patient's mouth to thereby eventually fill the lungs of the patient. Additionally, exhaled air or body secretions from the patient are diverted away from the patient's face by means of the ventilation/exhalation valve assembly 40. After use, the device is disposed of in the common waste.

As best shown in FIGS. 2, 3a–3b and 4, this CPR barrier device 10 generally includes the inflatable portion 12, an inflation member 30, the ventilation/exhalation valve assembly 40, and preferably, a barrier member 50. The inflatable portion 12 when inflated extends in the breathing direction between the rescuer 5 and the patient 7 so as to be placed around at least one breathing organ of the patient, such as the patient's mouth. The inflation member 30 receives airflow from the rescuer to inflate the inflatable portion 12. The ventilation/exhalation valve member 40 permits airflow from the rescuer to the patient while at the same time preventing the patient's exhalation and/or bodily fluids from reaching the rescuer. In order to prevent contaminants from reaching the rescuer, the barrier member 50 provides an additional shield between the rescuer and the patient. Each of the inflatable portion 12, inflation member 30, ventilation/exhalation valve member 40, and barrier member 50 will be described in more detail below.

Figure 3B:
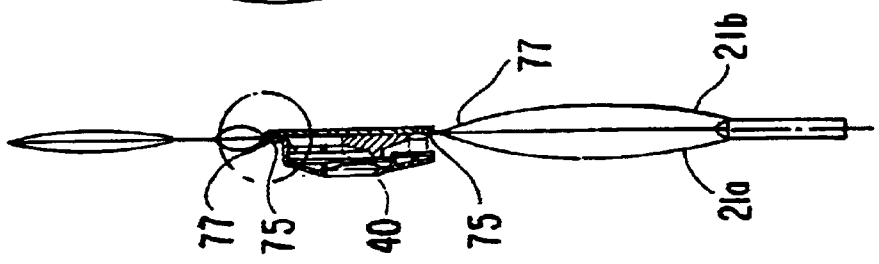
Figure 4:
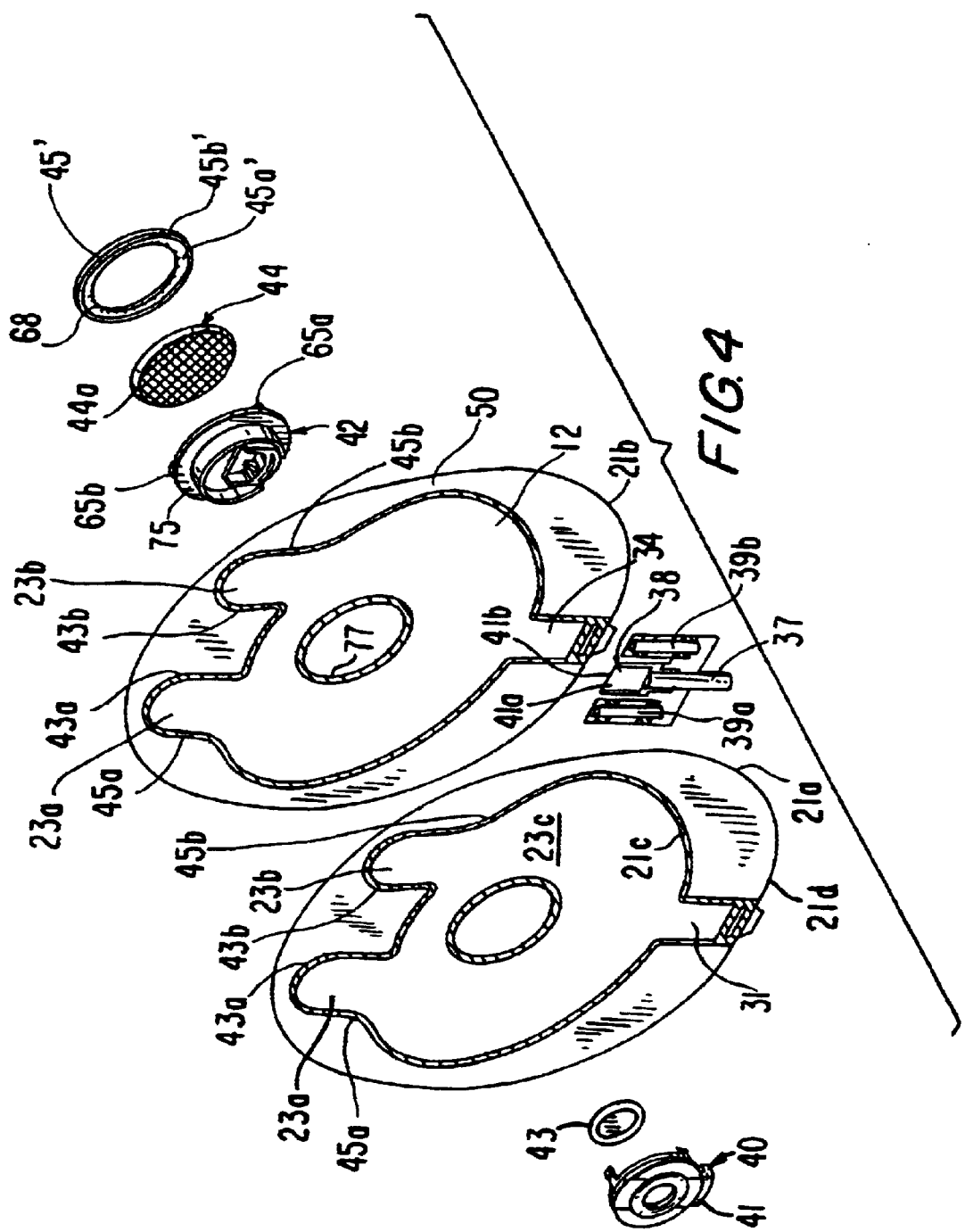
FIG. 4 is a front exploded perspective view of the CPR barrier device of FIG. 2.

As shown in FIGS. 3b and 4, the inflatable portion 12 and the barrier member 50 are formed of two sheets of flexible plastic film or membrane 21a and 12b. Preferably, the sheet membranes 21a and 21b are formed of flexible PVC film and are formed together at separation boundary 21c and at barrier edge 21d by welding processes, such as dielectric welding or RF frequency welding. Here, a die tool comes down and sandwiches and welds the PVC films together at the separation boundary 21c and barrier edge 21d.

As illustrated in FIG. 3a, when assembled, the sheet members 21a and 21b within the confines of the separation boundary form an air chamber 22 therebetween. The air chamber 22 when inflated forms a pillow-like member which can be placed around the mouth of the patient. The air chamber 22 of the inflatable portion 12 also includes nose pinch elements 23a and 23b to be described in more detail below which when inflated extend inwardly so as to be in a position to pinch the nostrils of the patient when the CPR barrier device is properly oriented on the patient.

As aforementioned, the inflatable portion 12, including the nose pinch elements 23a and 23b, is inflated by means of the inflation member 30 which receives airflow from the rescuer. As shown in FIGS. 2 and 3a, the inflation member 30 extends generally perpendicular to the breathing direction of the rescuer when inserted within a channel 34 of the air chamber 22. When so inserted, the inflation member 30 and the channel 34 permit air to flow from the rescuer to the air chamber 22 to inflate the same.

Figure 5:
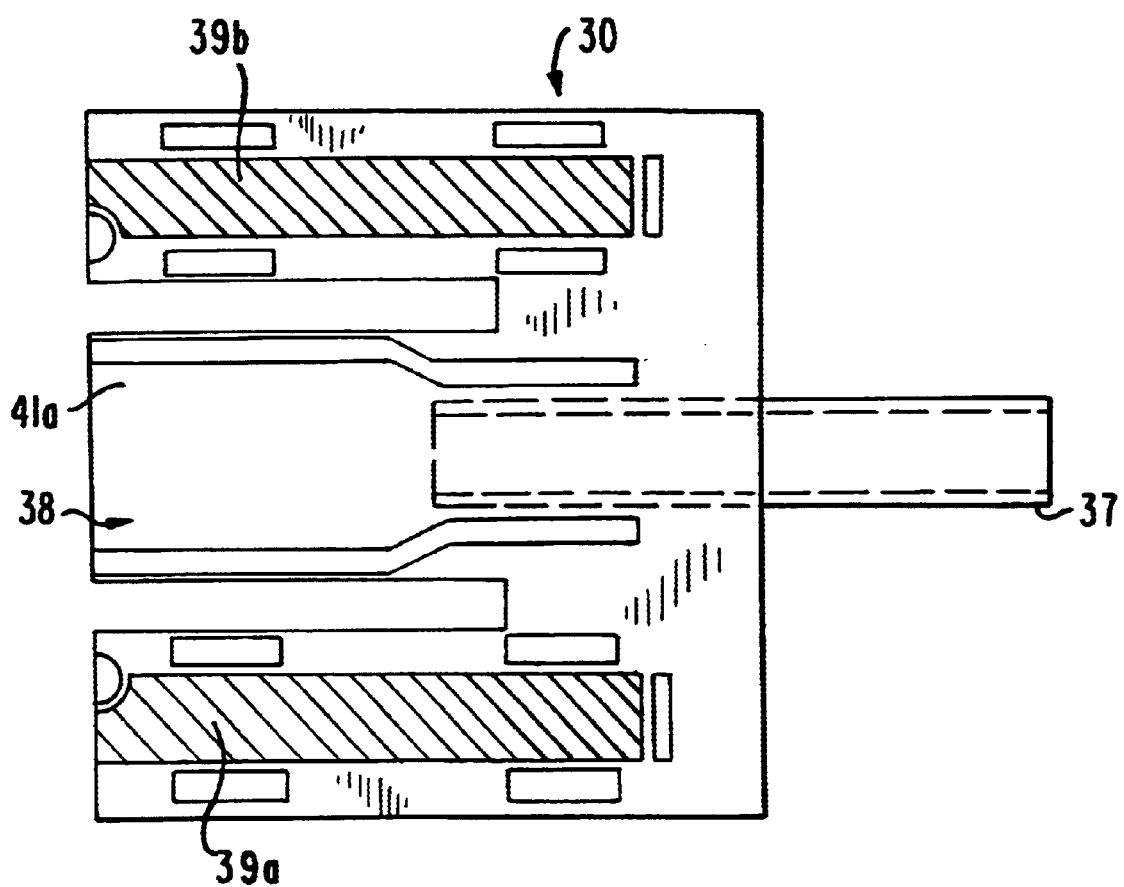
FIG. 5 is a top view of a preferred embodiment of the inflation valve member of the CPR barrier device of FIGS. 2 and 3a–b.

The inflation member 30 is welded into the membrane sheets 21a and 21b by means of dielectric welding or PF frequency welding. As will be explained in more detail below, when the CPR barrier device is removed from its case, the CPR barrier device is folded such that the inflation member is presented to the rescuer for inflation without any unfolding of the CPR barrier device. In the preferred embodiment of FIGS. 2 and 5, the inflation member 30 is formed of a relatively rigid yet flexible blow tube section 37, and a valve flap member section 38 extending from the blow tube section 37 and which is inserted into the channel 34 of the inflatable member 12, and a pair of stiffening rod members 39a and 39b which are welded to the membrane sheets 21a and 21b on opposite sides of the blow tube section 37, and the valve flap member section 38.

With this configuration, the inflation member 30 acts as a second valve member to permit airflow from the rescuer to pass into the air chamber 22 but prevents air from escaping from the air chamber 22 when the inflatable member 12 is properly inflated. More specifically, the flap member section 39 includes a pair of valve flap members 41a and 41b which open up when the rescuer blows air through the blow tube section 37 so as to inflate the air chamber 22. When the air chamber is sufficiently inflated, the back pressure of the air chamber 22 causes the flap members 41a and 41b to close upon each other to thereby provide an air tight seal to retain the inflatable portion 12 in its inflated condition and thereby prevent leakage of air from the inflatable portion 12 through the inflation member 30.

In addition, the stiffening rod members 39a and b provide a strengthening function to permit the inflation member 30 to be presented in a relatively rigid stable condition for handling and inflation when the CPR barrier device is deployed from its packaging.

Thus, the inflatable portion 12 is inflatable between an uninflated condition (see FIG. 2), wherein the CPR barrier device 10 is capable of lying generally flat on the face of the patient over at least one breathing organ of the victim, and an inflated condition (see FIGS. 3a–3b), wherein the inflatable portion 12 is inflated in the breathing direction between the rescuer and the patient so as to be placed around at over one breathing organ of the patient. As a result, the CPR barrier device of this invention permits mouth-to-mouth resuscitation to occur in both the uninflated and inflated conditions of the inflatable portion 12.

Figure 6A:
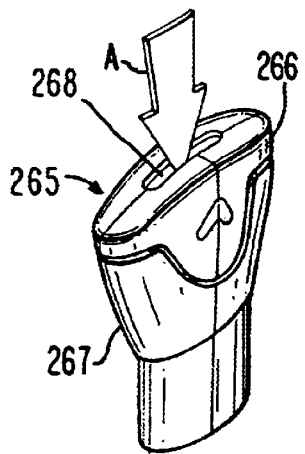
FIGS. 6a–e are various views explaining the operation of another preferred embodiment of an inflation valve member which can be used in conjunction with the CPR barrier device of the present invention.
Figure 6B:
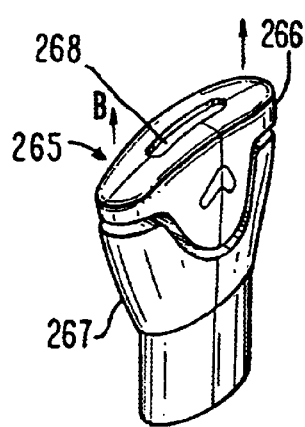
Figure 6C:
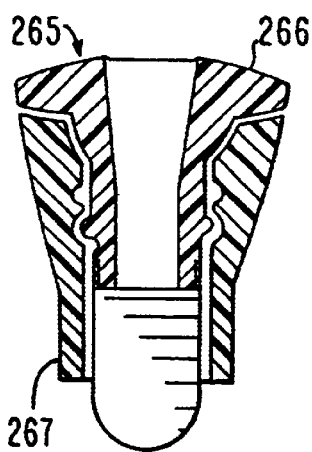
Figures 6D, 6E:
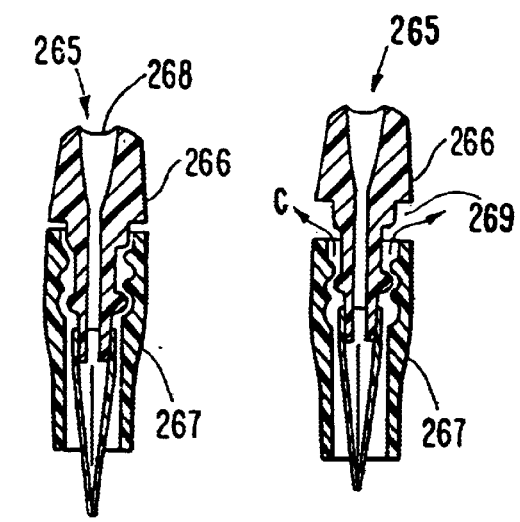
Figure 7A:
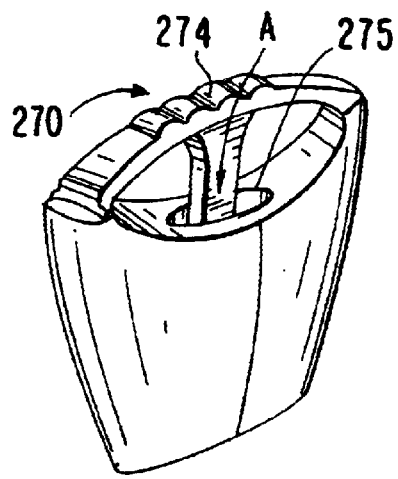
FIGS. 7a–d are various views explaining the operation of another preferred embodiment of an inflation valve member which can be used in conjunction with the CPR barrier device of the present invention.
Figure 7B:
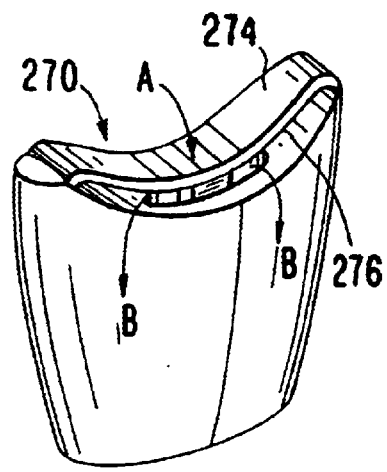
Figure 7C:
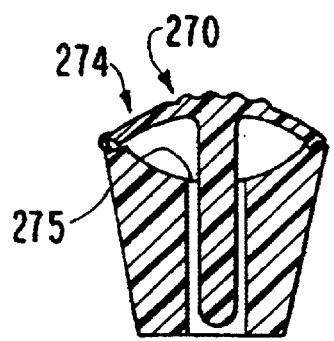
Figure 7D:
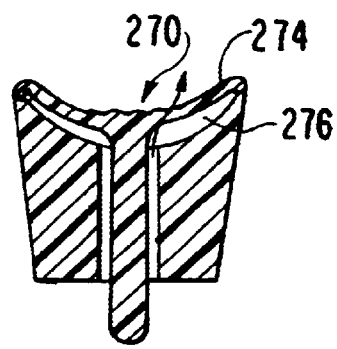
Figure 8A:
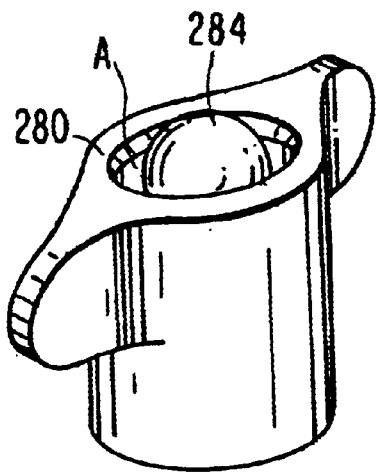
FIGS. 8a and 8b are front perspective views of yet another inflation valve member which can be used in conjunction with the CPR barrier device of the present invention.
Figure 8B:
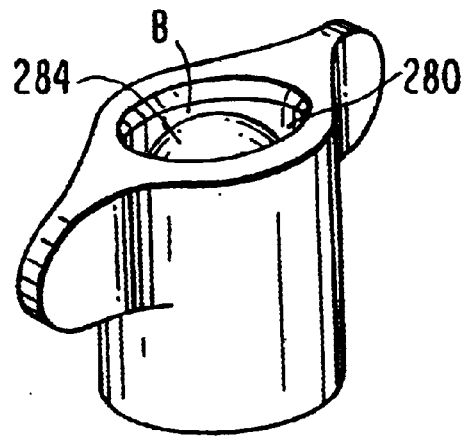
Figure 8C:
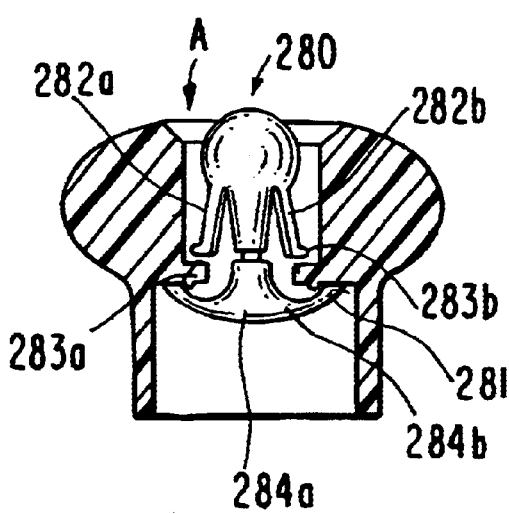
FIGS. 8c and 8d are front sectional views of the inflation valve member of FIGS. 8a and 8b.
Figure 8D:
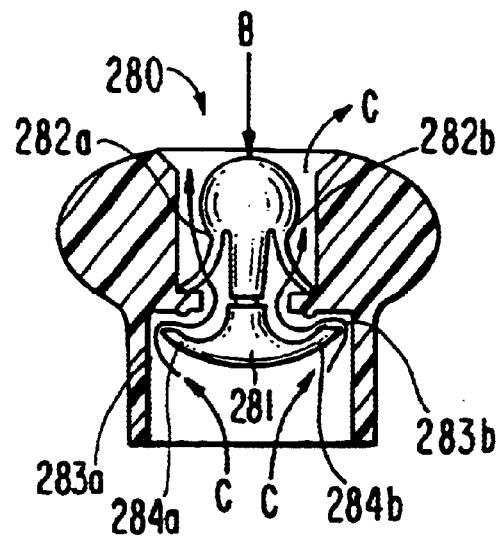
Figure 10:
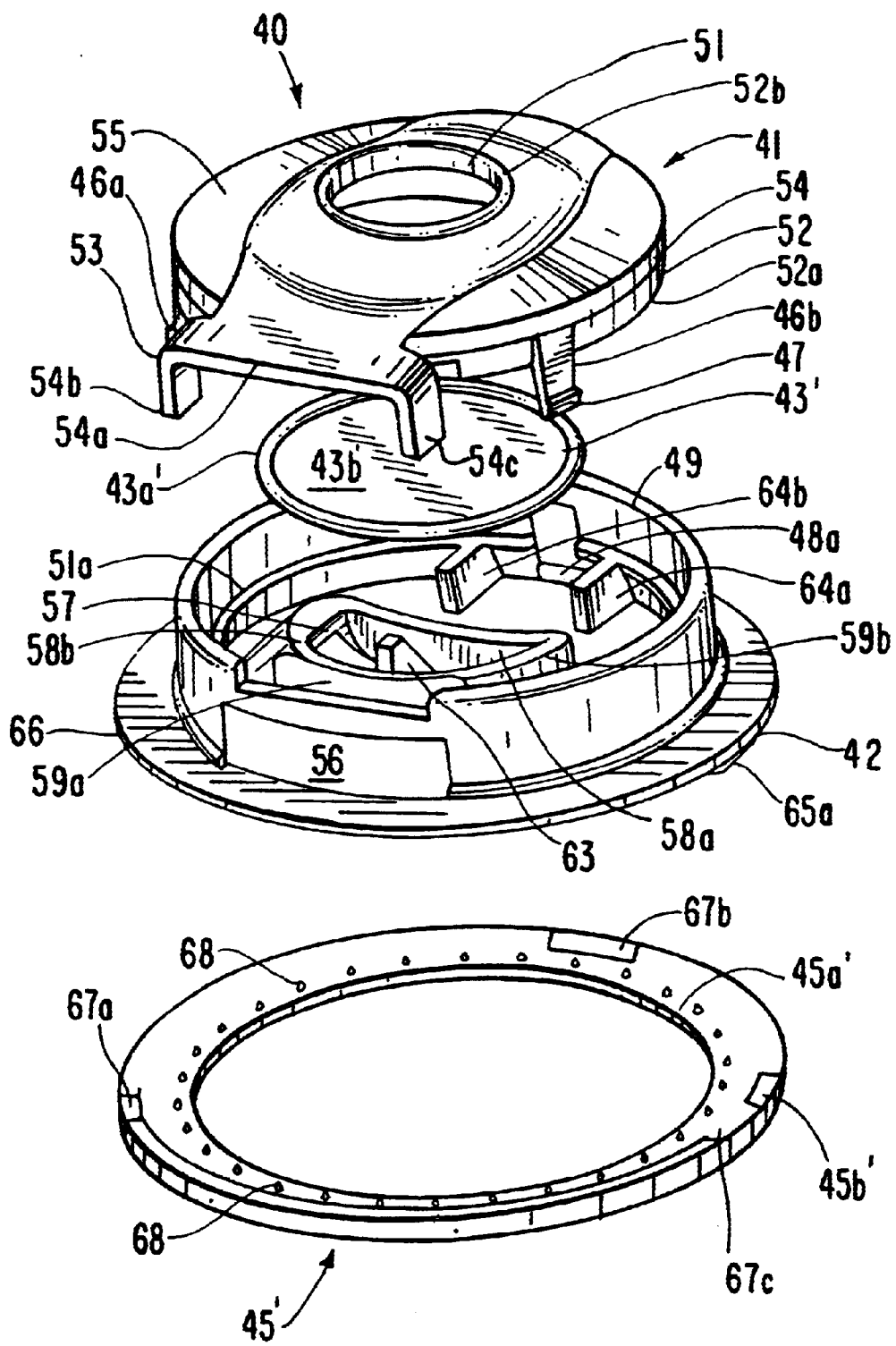
FIG. 10 is an enlarged perspective exploded view of the ventilation/exhalation valve assembly of the CPR barrier device of FIGS. 2 and 3a–3b.

Various other inflation members which can be substituted for the inflation member 30 to inflate the inflatable portion 12 of the CPR barrier device of the present invention are shown in FIGS. 6a–6e, 7a–7d, 8a–8d and 9a–9b of this application. These include a pull-out valve 265 (see FIGS. 6a–6e), a plunger valve 270 (see FIGS. 7a–7d), an umbrella valve 280 (see FIGS. 8a–8d), and a pop-up duckbill valve 285 (see FIGS. 9a–9b). As best shown in FIGS. 6a–6b, the pull-out valve 265 is in the form of a film valve. The film valve is a solid one-piece molded component made of PVC so that it is compatible with the inflatable portion material. When it is desired to inflate the air chamber 22, the male member 266 of the pull-out valve is pushed in so that there is no gap 269 between the male member 266 and the female valve seat 267 of the pull-out valve 165 (see FIGS. 6a–c). As a result, the rescuer's air is blown in through opening 268 in the direction of arrow A. The film valve is self-closing. As air pressure within the air chamber increases, back pressure is placed on the valve which will the further seal the film. In order to deflate the air chamber 22, the male member 266 is pulled outwardly in the direction of arrows B in FIG. 6b disengaging the male member 266 from the female valve seat 267 such that the gap 269 is created therebetween such that air escapes from the air chamber 22 therethrough (see arrow C in FIG. 6e).

The operation of the plunger valve 270 is shown in FIGS. 7a–7d of this application. The plunger valve 270 is molded as one piece and then slits are put in as a secondary operation. In order to inflate the air chamber, the flexible arm 274 on the plunger valve 270 is bowed outwardly (see FIGS. 7a and 7c). Thus, the air chamber is inflated by the rescuer blowing air in the direction of arrow A through opening 275. Back pressure within the air chamber causes the flexible arrows to close upon themselves to seal the air openings. In order to deflate the air chamber, the flexible arm 273 is bowed inwardly and air from the inflatable portion is exhausted through lateral air openings 276 in the direction of arrows B (see FIG. 7b).

The operation of the umbrella valve 280 is best shown in FIGS. 8a–8d. This umbrella valve 280 includes a valve seat 281 and flexible arms, such as 282a and 282b (see FIGS. 8a and 8c). In order to inflate the air chamber 22, the knob 284 of the umbrella valve 280 is lifted upwardly (see FIGS. 8c and 8d). This results in openings 283a and 283b being created between the flexible arms 282a and 282b and the flange members 284a and 284b of the valve seat 281 such that air from the rescuer can be blown into the air chamber 22 in the direction of arrow A (see FIG. 8c). In order to deflate the air chamber 22, the knob 284 is pushed inwardly in the direction of arrow B (see FIGS. 8b and 8d) such that the openings 283a, 283b are closed and air is exhausted from the inflatable portion through arrows C.

The operation of the pop-up duckbill valve 285 is shown in FIGS. 9a and 9b. In the non-use position, the pop-top duckbill valve 285 is retained in a recess 286 of the ventilation/exhalation valve 286a to be described in further detail below. In order to inflate the air chamber, the pop-up duckbill valve 285 is removed from recess 286 and bent along hinge 287. A locking cap 289 of the pop-up duckbill valve 285 includes flexible arms 288a, 288b which open and close the duckbill valve. In order to inflate the air chamber 22, the locking cap is in an orientation such that the flexible arms 288a, 288b close the valve. In order to deflate the air chamber, the flexible arms 288a and 288b are pinched inwardly in the direction of arrows A in FIG. 9b opening the duckbill valve opening 299.

In order to assist the rescuer in sealing the nose of the patient, the inflatable portion 12 of the CPR barrier device of the present invention may also include nose pinch elements 23a and 23b which extend as thumb-like projections from the central portion 23c of the inflatable portion opposite to the air channel 34 (see FIGS. 2, 3a and 4). Upon inflation of the inflatable portion 12, the inner edges 43a and 43b of the respective nose pinch elements 23a and 23b are positioned to be aligned adjacent to the nostrils of the patient to assist the rescuer in closing the nasal air passages. In addition, the nose pinch elements 23a and 23b are designed so as to provide a cushion effect to brace the patient's nose when the rescuer applies a pinching force along outer edges 45a and 45b thereof. Therefore, less pressure is required by the rescuer to close the nasal air passages. In this manner, the nose pinch elements permit indirect squeezing of the nose by the rescuer.

When inflated, the nose pinch elements 23a and 23b form a three-dimensional tent which conforms the CPR barrier device to the contour of the patient's face. With this three-dimensional tent, the nose pinch elements 23a and 23b are positioned on opposite sides of the nose and a tent covering 47 is formed in the barrier member 50 so as to be provided between the nose pinch elements 23a and 23b to provide a narrowed bridge to be positioned over the nose of the patient and properly orient the CPR barrier device thereon. In addition, the three-dimensional tent with inwardly extending inflated nose pinch elements 23a and 23b causes the CPR barrier device to be wider at its base 51 (adjacent the inflation member 30) than at the top portion thereof (adjacent the nose pinch elements 23a and 23b). Therefore, the CPR barrier device naturally conforms to the face of the patient when inflated as the chin of the patient is covered but yet the eyes of the patient are exposed. Thus, the nose pinch elements further assist the rescuer in properly orienting the CPR barrier device on the face of the patient.

As shown in the embodiment of FIGS. 10–16, the ventilation/exhalation valve assembly 40 is in the form of a one-way valve which allows air to flow from the rescuer to the patient but prevents the patient's exhalation and bodily fluids from reaching the rescuer. The ventilation/exhalation valve member 40 includes a top housing 41, a bottom housing 42, a flexible diaphragm 43, a filter 44a and a filter retaining ring 45.

In order to secure the upper and lower housings 41 and 42 of the ventilation/exhalation valve member 40, the upper housing 41 has a plurality of downwardly depending legs 46a, 46b and 46c having a camming mating engagement portion 47 at the edge thereof. The lower housing 42 has a plurality of mating recesses or grooves, such as 48a in FIG. 10, formed in the generally cylindrical main member 49 thereof such that that camming mating engagement portions 47 of the downwardly legs 46a, 46b and 46c are respectively engaged in the mating recesses, such as 48a, so as to retain the upper housing 41 with respect to the lower housing 42.

The generally cylindrical main member 49 also includes an inwardly extending ledge member 51a on which the bottom surface 52a of the downwardly extending circumferential edge 52 of the top housing 41 rides so as to provide an air seal between the top and bottom housings 41 and 42. The circumferential edge 52 of the top housing 41 also includes a projecting edge section 54 (see FIG. 12) circumferentially extending outwardly thereof so as to abut against the inner surface of the lower housing main member 49 and thereby provide an additional air seal between the upper and lower housings 41 and 42. In cross-section, this projecting edge section 54 is of a saw-tooth like form and acts as an O-ring. During ventilation, the hoop tension on the projecting edge section 54 closes the gap formed between the upper and lower housings to maintain a seal between the two housings.

Figure 12:
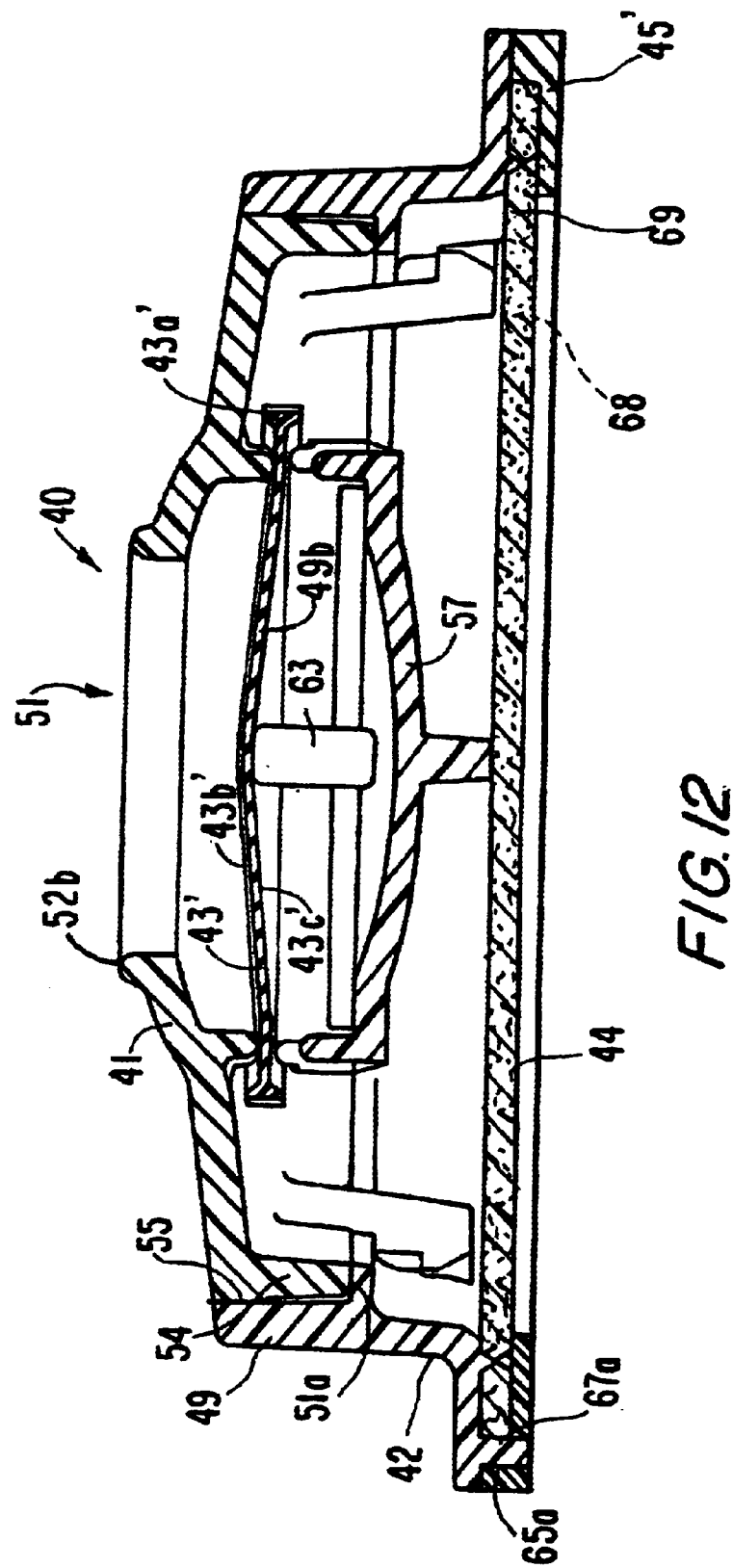
FIG. 12 is a front sectional view of the ventilation/exhalation valve assembly of FIG. 10.

FIG. 12 further illustrates that the upper housing 41 includes a upper mouthpiece opening 51 through which the rescuer blows air therethrough to ventilate the patient. The upper opening 51 has a mouthpiece-type contoured rim section 52b surrounding it to conform to the general contour of the rescuer's mouth.

Figure 14:
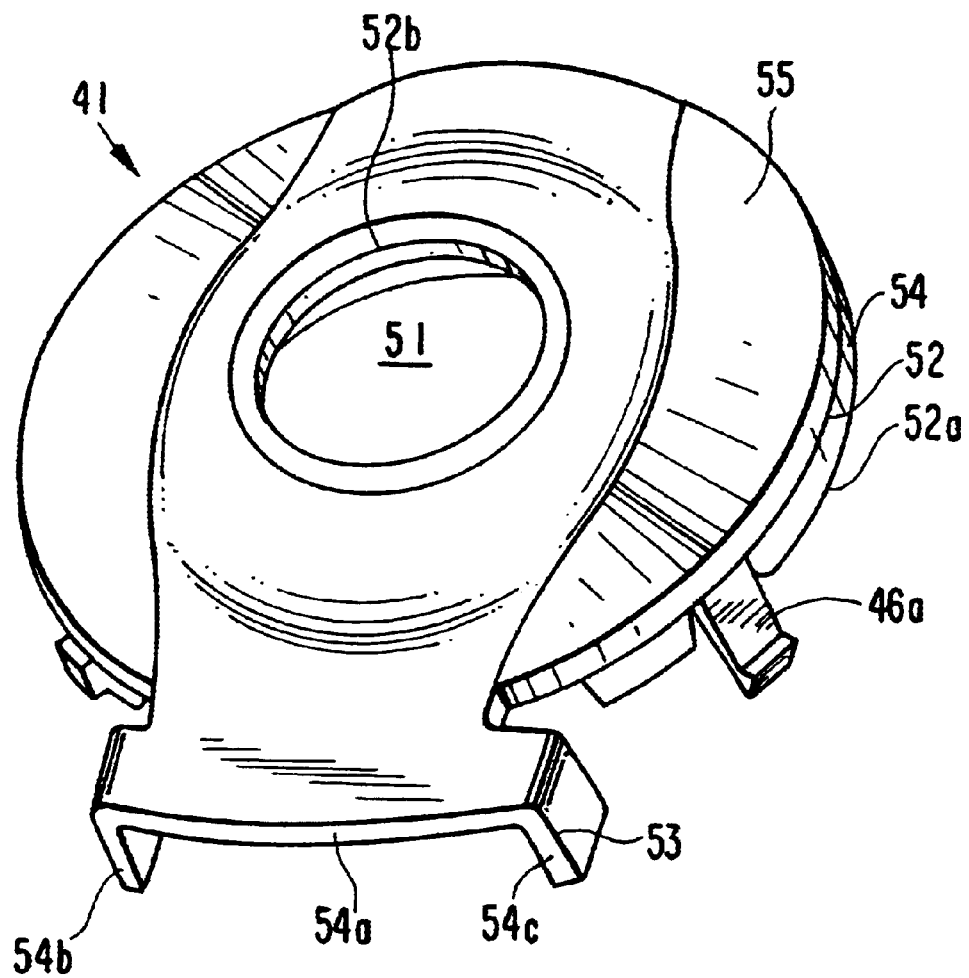
FIG. 14 is a top perspective view of the top housing of the ventilation/exhalation valve assembly of FIG. 10.
Figure 15:
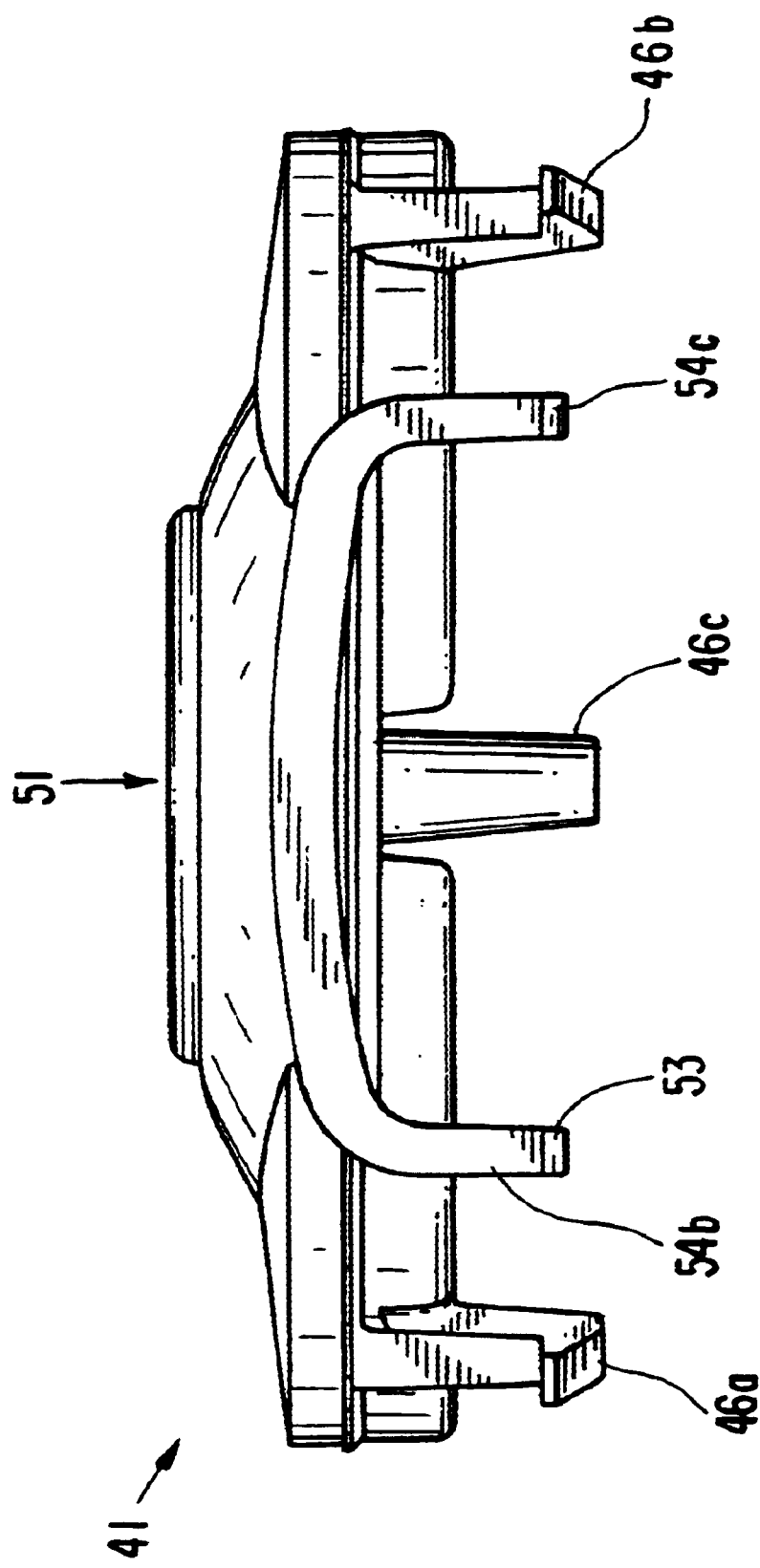
FIG. 15 is a front elevational view of the top housing of FIG. 14.

The upper housing 41 further includes an exhalation diverter flange member 53 which diverts the patient's exhalation and undesired bodily fluids away from the rescuer. As is best shown in FIG. 14, the exhalation diverter flange member 53 is generally inverted U-shaped with a top cover 54a and two side legs 54b and 54c depending downwardly from the top cover 54a. The diverter flange member 53 extends from the main section 55 of the upper housing 41 such that when the upper housing 41 is secured to the lower housing 42, the diverter flange member 53 surrounds the exhalation opening 56 provided in the lower housing main member 49. As a result and as will be described in more detail below, the patient's exhalation and bodily fluids passing through the exhalation opening 56 is diverted away from the rescuer.

Figure 16:
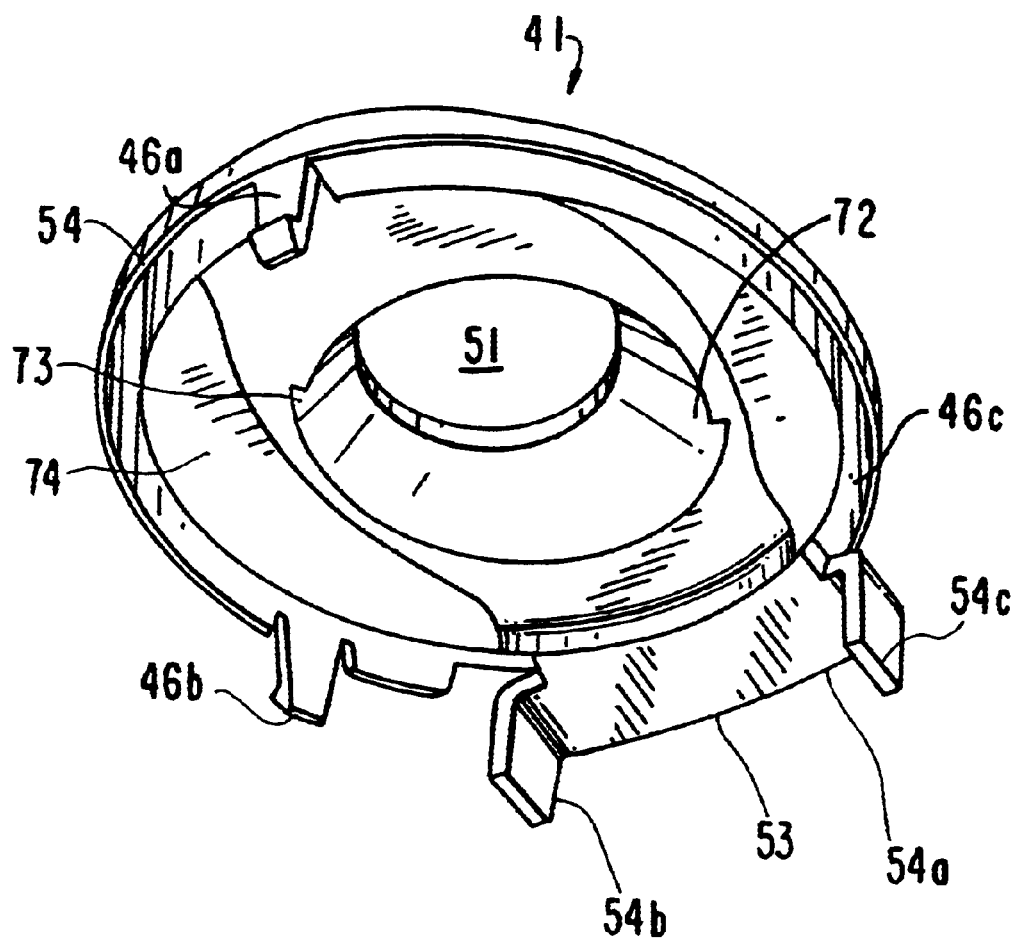
FIG. 16 is a bottom perspective view of the top housing of FIG. 14.

In addition, a generally cylindering retaining rim 72, which surrounds the upper opening 51, extends downwardly from the bottom surface 74 of the top housing 41 (see FIG. 16). When the flexible diaphragm 43 is in its proper orientation between the first and second housings 41 and 42, the retaining rim 72 provides for the upper retention of the flexible diaphragm 43 therewithin and prevents the flexible diaphragm from further upward movement during exhalation by the patient.

The lower housing 42 of the ventilation/exhalation valve member 40 includes a diaphragm support structure 57 extending inwardly from the lower housing main member 49. The diaphragm support structure 57 supports the flexible diaphragm 43 in its proper orientation when the upper housing 41 is secured to the lower housing 42. The diaphragm support structure 57 includes a first base member 58a and a second base member 58b at a horizontal plane above the horizontal plane of the first base member 58a. The second base member 58b has a first generally arcuate-shaped rim 59a and a second generally semi-circular-shaped rim 59b extending therefrom.

Figure 13:
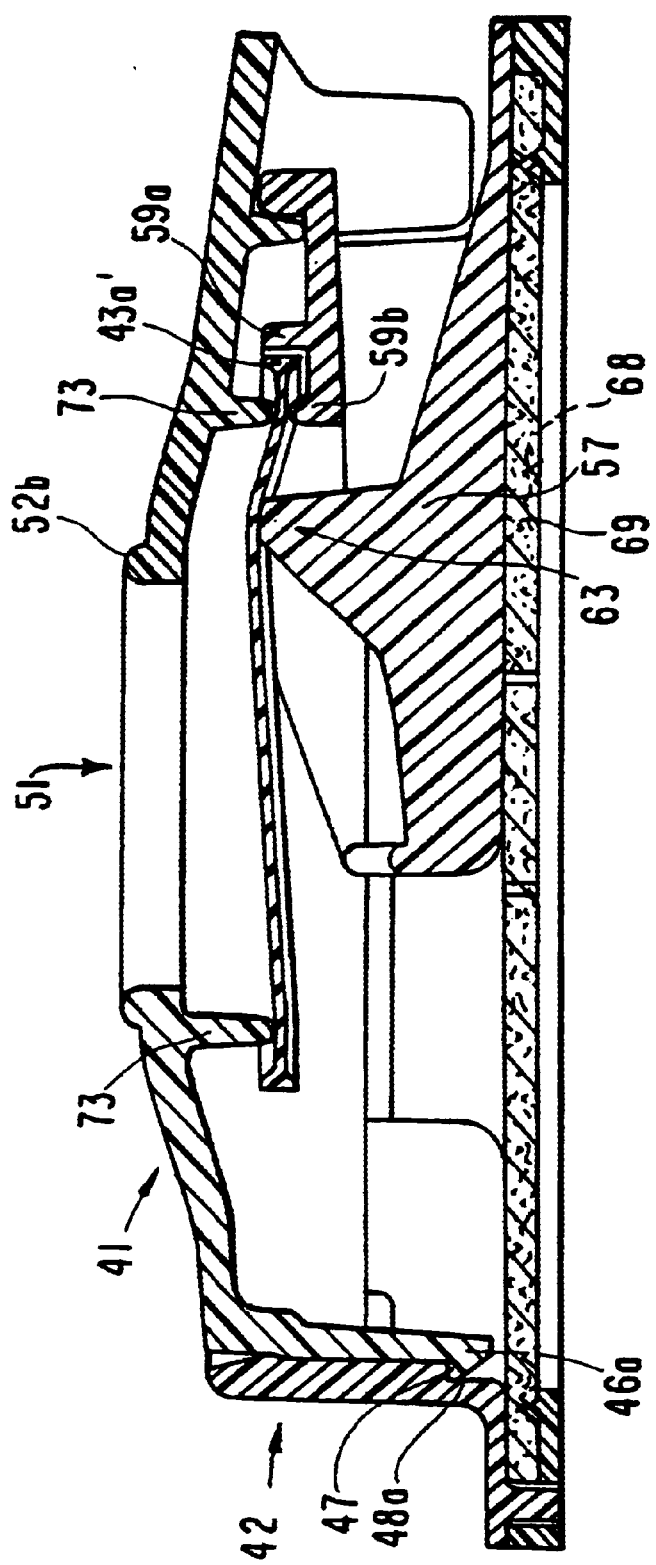
FIG. 13 is a side sectional view of the ventilation/exhalation valve assembly of FIG. 10.

As is best shown in FIG. 13, the flexible diaphragm 43 is positioned between the upper and lower housings 41 and 42 such that the outer peripheral edge 43a thereof abuts against the first generally arcuate-shaped rim 59a and the bottom surface 43c of the central portion 43b rests on the second generally semi-circular shaped rim 59b. The first base member 59a includes an inclined ramp camming edge 63 which abuts against the bottom surface 43c of the central portion 43b of the flexible diaphragm 43 and provides a fulcrum point for a cantilever-type deflection of the flexible diaphragm during ventilation by the rescuer. In addition, the inclined ramp camming edge 63 preloads the flexible diaphragm 43 and pushes the diaphragm against the retaining rim 73 of the upper housing 41 to assure a proper seal during exhalation by the patient. In order to properly ventilate, the rescuer must overcome this preload.

The lower housing 42 further includes two rib members 64a and 64b which extend inwardly from the lower housing main member 49 across from the diaphragm support structure 57. These ribs 64a and 64b prevent the rescuer from pushing his/her fingers through the ventilation/exhalation valve assembly 40.

The filter assembly 44 of the ventilation/exhalation valve assembly 40 includes a filter 44a and the filter retaining ring 45. The filter 44a not only filters the rescuer's air during ventilation but always filters exhalation and bodily fluids of the patient during exhalation so as to reduce the chances of contaminants affecting the operation of the ventilation/ exhalation valve assembly and reaching the rescuer. The filter 44a is preferably made of a substantially opaque, porous material. The filter 44a is placed on top of the upper ring surface 45a of the filter retaining ring 45 such that the filter is positioned within the circumferential flange 45b of the ring 45. The bottom surface 66 of the lower housing 42 includes a plurality of downwardly extending stepped legs, such as 65a and 65b, which are engaged with ring notches, such as 67a, 67b and 67c of the filter retaining ring (see FIG. 17), so as to mechanically secure and lock by a press fit the filter assembly to the lower housing. In order to provide for further securement, the filter retaining ring 45 is RF welded to the lower housing 42. Tooth-like projections 68 extend upwardly from the upper ring surface 45a of the retaining ring 45 and tooth-like projections 69 extend downwardly from the bottom surface 66 of the lower housing 42 with both respective projections 68 and 69 extending into the filter 44 to retain the filter 44 in its desired orientation within the ventilation/exhalation valve member 40.

As is shown in FIG. 3b, the ventilation/exhalation valve assembly 40 is secured to the inflatable member 12 as the upper surface 75 of the cylindrical base flange 76 of the lower housing 42 is RF welded to the inner boundary seam 77 of the inflatable member.

Figure 17:
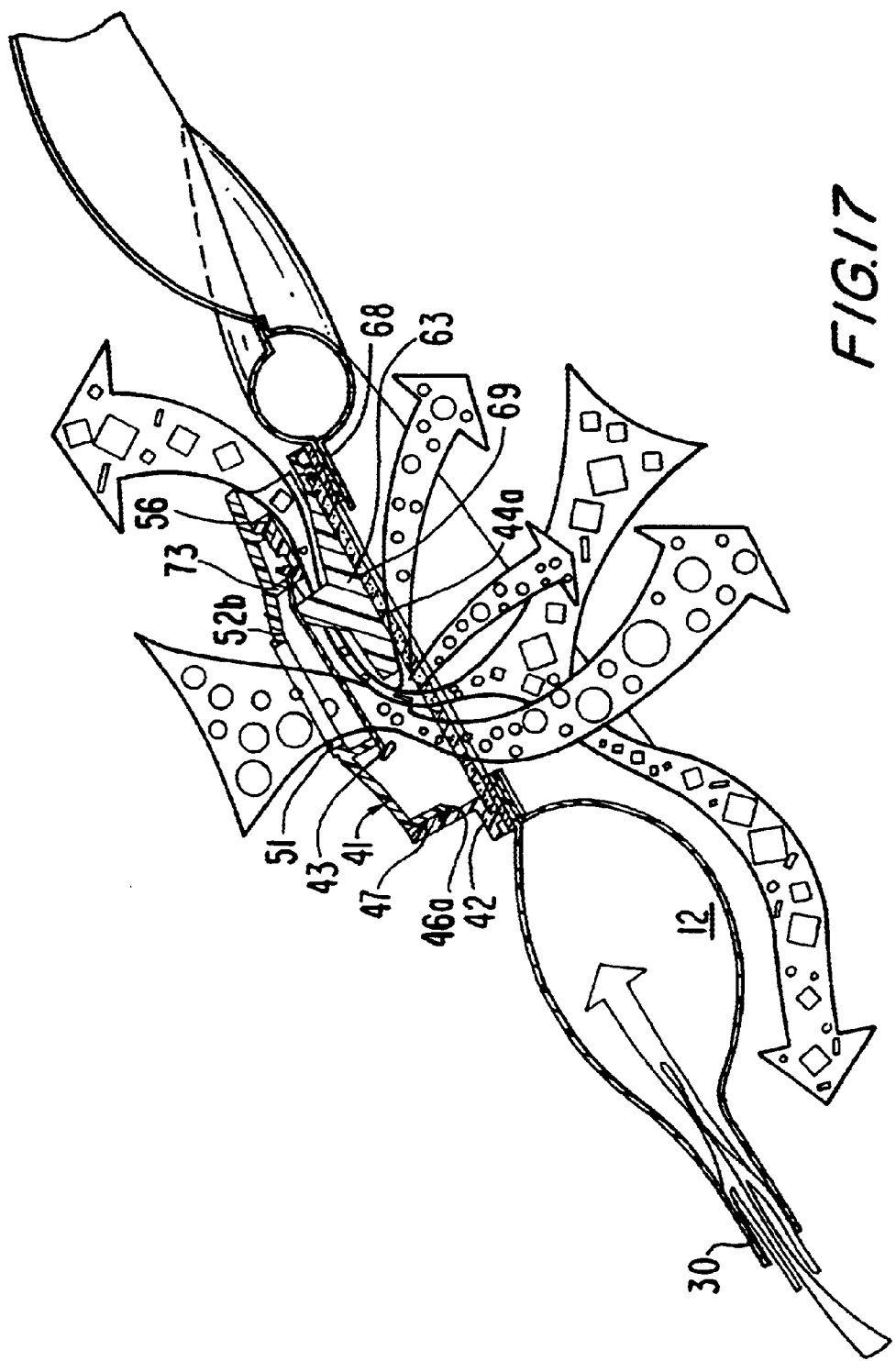
FIG. 17 is a front section view of the valve assembly of FIGS. 10–16 specifically illustrating the flow of rescuer ventilation and patient exhalation.

In use, the ventilation/exhalation valve member 40 operates as shown in FIG. 17. The rescuer places his mouth around the contoured mouthpiece rim section 52b of the upper housing 41. The air flow from the rescuer passes through the upper mouthpiece opening 51 and deflects the flexible diaphragm 43 downwardly upon sufficient pressure applied thereto due to the preload applied by inclined ramp camming edge 63 of the lower housing 42. As a result, the diaphragm 43 is flexed so that air from the rescuer is passed through the filter 44a and in turn into the patient's breathing organ. Without any air pressure from the rescuer, the flexible diaphragm 43 springs back to its natural position sealed against the upper housing 41 and thereby covering the mouthpiece opening 51. Therefore, exhalation from the patient always passes through the filter 44a and stays underneath the flexible diaphragm 43 and is diverted from the ventilation/exhalation valve assembly 40 through the exhalation diversion opening 56 provided in the lower housing 42. Since the diverter flange member 53 of the upper housing 41 surrounds the exhalation opening, the ventilation/exhalation valve member 40 of the present invention diverts the patient's exhalation and bodily fluids away from the rescuer.

In order to further shield the rescuer from the patient, the barrier member 50 may be incorporated in the CPR barrier device of the present invention. This barrier member 50 is RF welded to the inflatable portion 12 at the outer boundary seam 21c of the inflatable portion 12. The barrier member 50 is configured so as not to cover the eyes but is of a greater width at the chin area so that the rescuer can grab the jaw portion of the barrier member 50 of the patient to attempt to open the victim's airway in this manner without touching the patient. The barrier member 50 also includes wider areas 78a and 78b (see FIG. 2) which are provided adjacent to the respective nose grip elements 23a and 23b to provide a pinching surface for the rescuer to apply inward force to the outer peripheries 45a and 45b of the nose grip elements 23a and 23b. Therefore, the barrier member 50 not only provides a shield for the rescuer from exhalation of the patient but also provides a hand gripping area to assist the rescuer in placement of the CPR barrier device on the patient.

Figure 18:
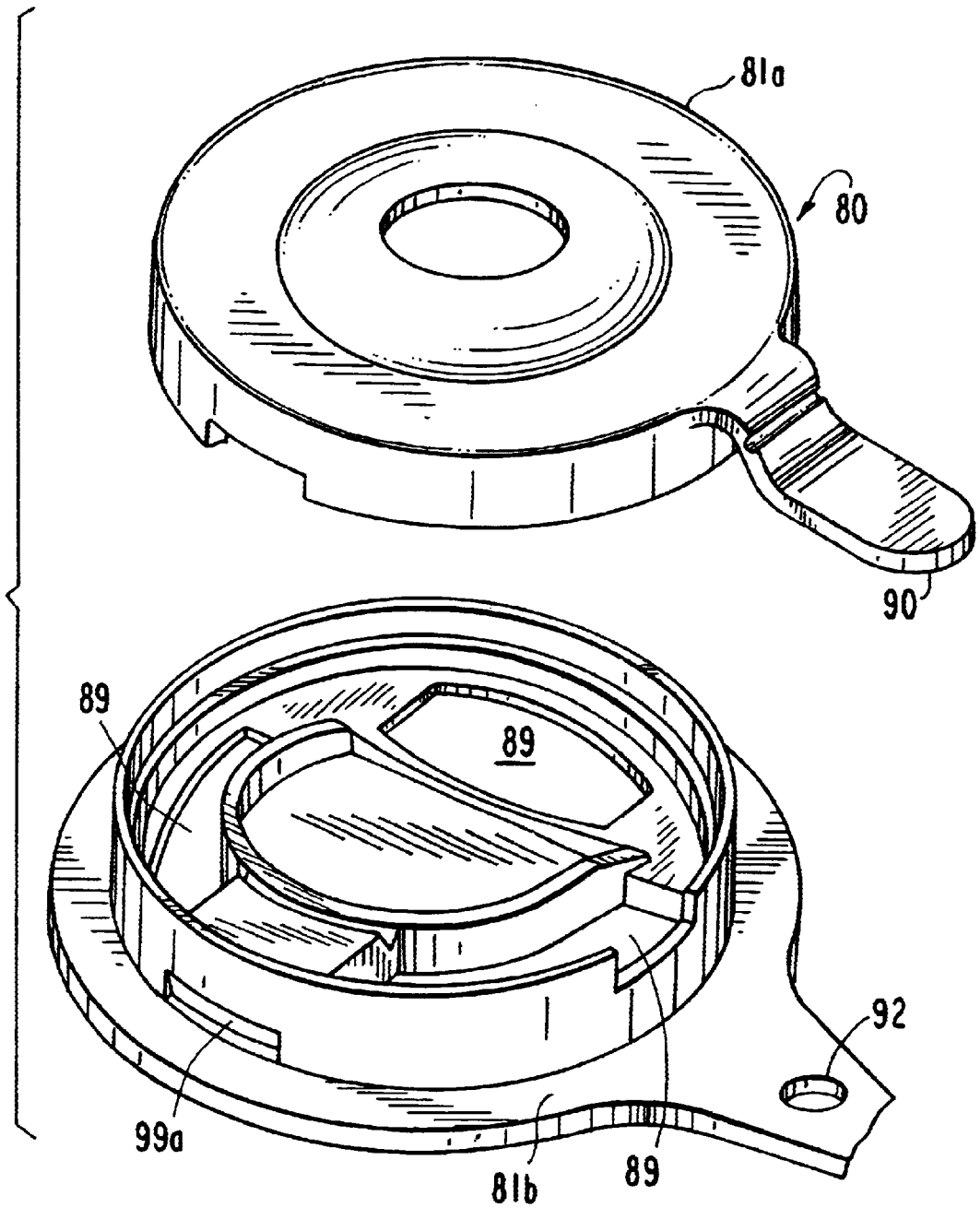
FIG. 18 is a top exploded perspective view of another preferred embodiment of a ventilation/exhalation valve assembly which can be incorporated in the CPR barrier device of the present invention.
Figure 19:
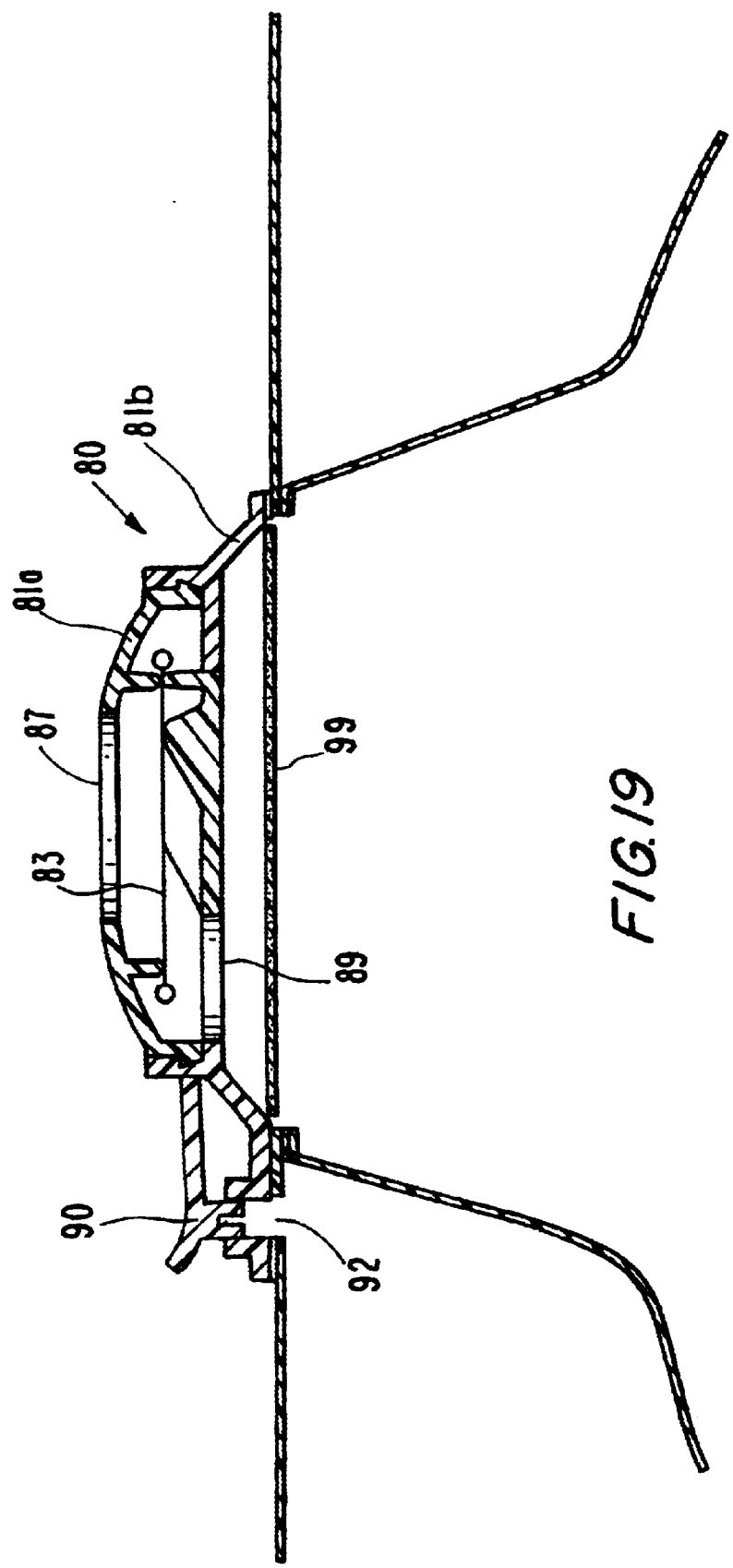
FIG. 19 is a side section view of the valve assembly of FIG. 18 with its lock member in a closed condition to allow inflation of the inflatable portion.
Figure 20:
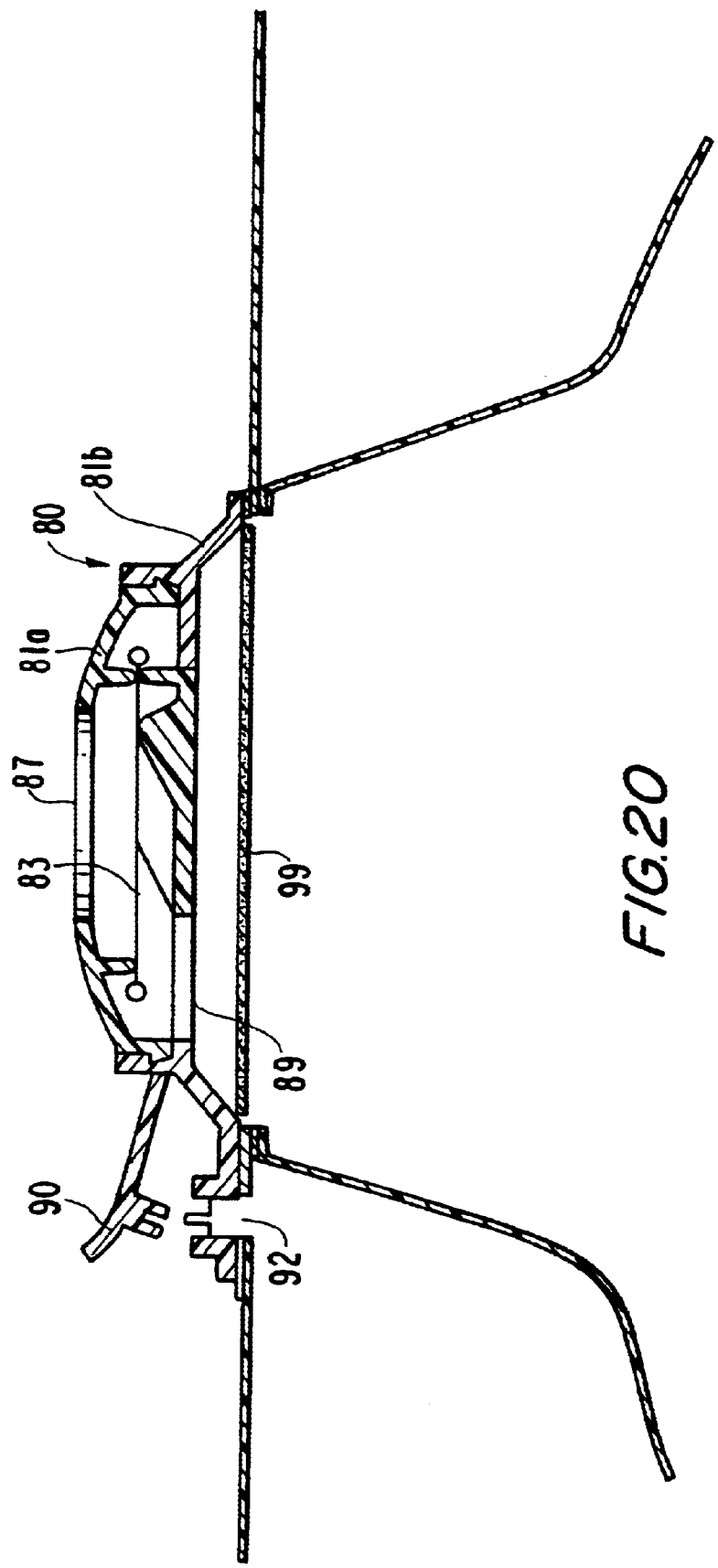
FIG. 20 is a side section view of the valve assembly of FIG. 19 with its lock member in an open condition.
Figure 21:
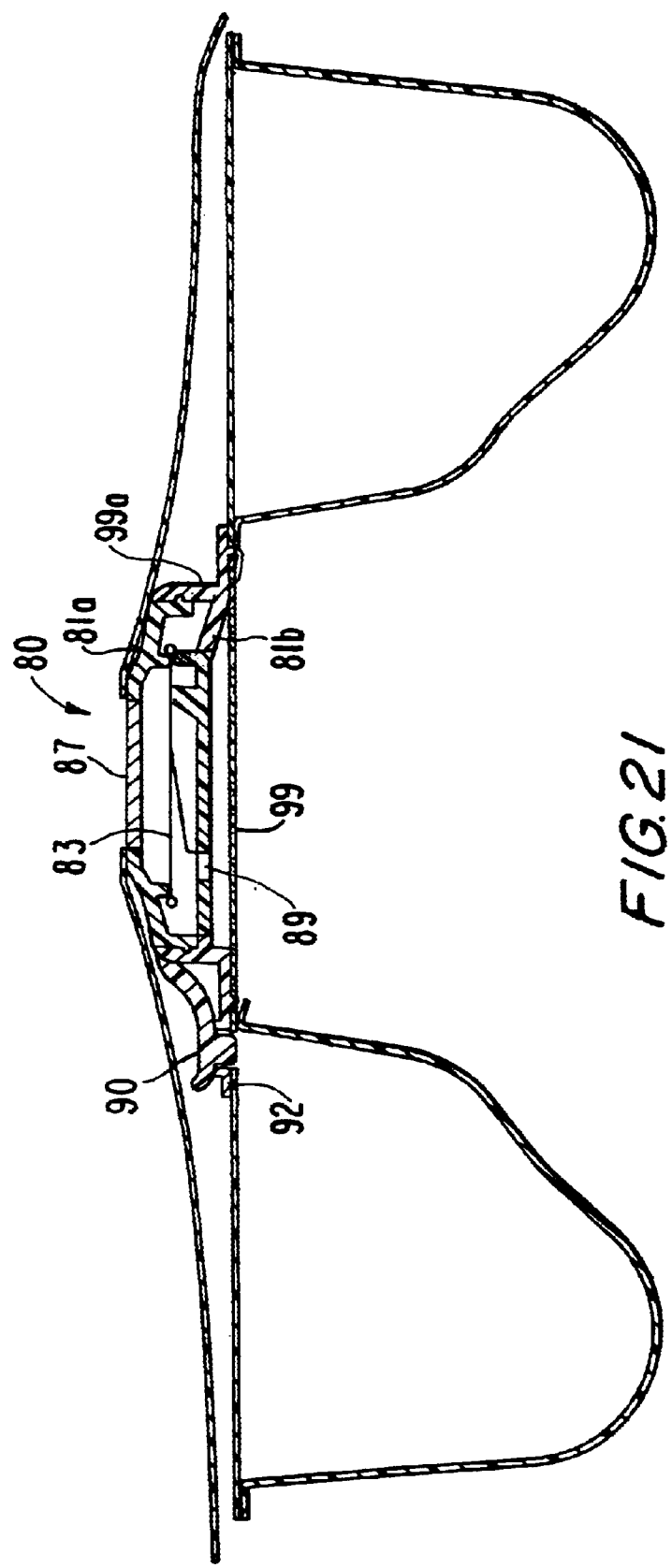
FIG. 21 is a side section view of the valve assembly of FIG. 18 with the lock member in its closed position to allow inflation of the inflatable portion.

Another preferred embodiment of a ventilation/exhalation valve member 80 which can be incorporated in the CPR barrier device of the present invention is shown in FIGS. 18 through 22. This ventilation/exhalation valve member 80 also provides a lock member for inflating, deflating the inflatable portion. As shown in FIG. 18, this valve member 80 is formed of a top housing 81a and a lower housing 81b. Deflation or inflation of the inflatable portion is achieved by the lock member which is preferable in the form of an inflation/deflation lock pin 90 extending from the top housing 81a. As is best shown in FIG. 20, when the lock pin 90 is disengaged from retention member 92 in the bottom housing 81b of the valve assembly 80, the inflatable cuff 98 can be deflated. However, when the lock pin 90 is engaged in the retention member 92 of the valve member 80 (see FIGS. 19 and 21), the inflatable portion can be inflated and remains so.

In the valve assembly 80 of FIGS. 18 through 22, a silicone diaphragm 83 is secured between the top and bottom housings 81a and below the rescuer side air passage 87. Ventilation is provided through the air passage 87 deflecting the silicone diaphragm 83 downwardly such that ventilation air passes through the victim air passage 89 through the filter 99 so as to be received by the victim (see arrow A in FIG. 22). During exhalation, the silicone diaphragm 83 returns to its generally horizontal position and traps the exhaled air therebeneath so that it does not pass through the rescuer air passage 87. Instead, the exhalation air passes around the inflatable cuff member 98 and secondarily through the filter member 99 and laterally outwardly of the ventilation/exhalation valve member 80 through lateral side air passages 99a (see arrows B in FIG. 22).

Another preferred embodiment of a ventilation/exhalation valve assembly which can be incorporated the CPR barrier device of the present invention and provides for further protection during patient exhalation is shown in FIGS. 23a and 23b. As shown in FIG. 23a, the valve assembly 101 is formed of an upper housing 102 and a lower housing 104 which has a patient exhalation barrier disk 105 held therebetween and a silicone diaphragm 103 contained between the upper and lower housings 102 and 104. The valve assembly includes an upper orifice 106 and a lower orifice 108. The rescuer blows into the orifice 106 such that the silicone diaphragm 103 is deflected downwardly as shown as position B in FIG. 23b so that the air passes through lower opening 108 and filter 109 such as to be received into the patient's lungs. During exhalation, the silicone diaphragm 103 returns to its generally horizontal position at position A to close the upper orifice 106 such that the patient's exhalation passes into the valve chamber 107 and is exhausted through lateral orifice 111 and passes underneath the patient exhalation barrier disk 105.

Figure 24:
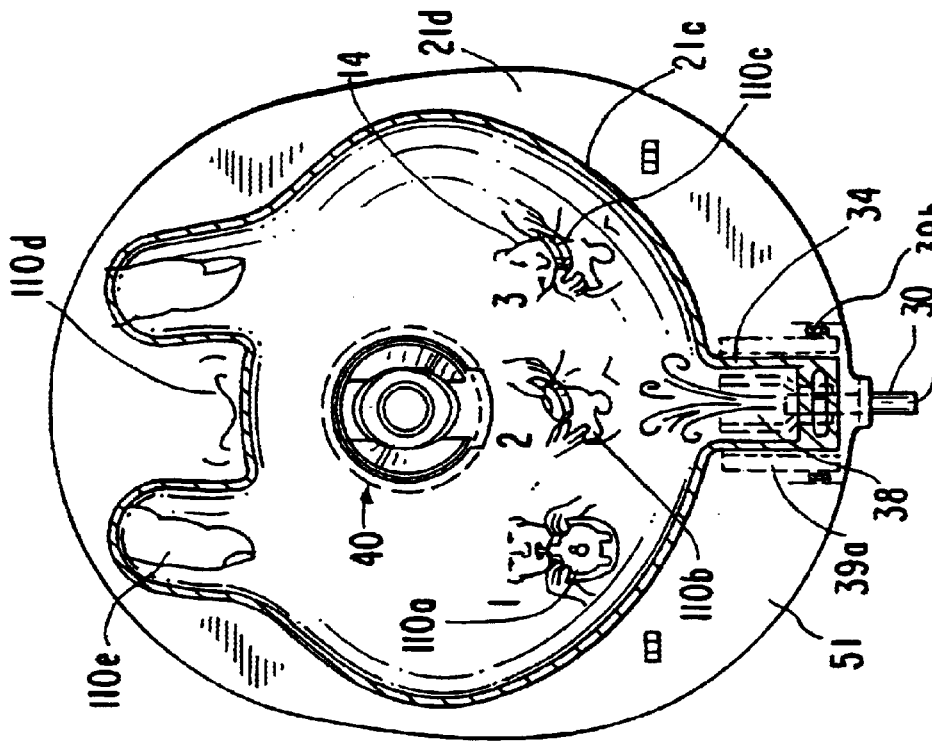
FIG. 24 is a top view of the CPR barrier device of FIG. 2 with identifying symbols and features.

The CPR barrier device of the present invention is also designed to permit certain CPR instructions to be placed on the rescuer's side of the barrier device. As shown in FIG. 24, these instructions can relate to the inflation of the inflatable portion by means of the inflation member (see instruction 110a), proper placement of the CPR barrier device on the victim (see instruction 110b), and proper ventilation by the rescuer (see instruction 110c). These instructions can also assist an inexperienced rescuer with proper positioning of the CPR barrier device on the patient. For instance, certain facial features of the patient, such as the nose 110d, can be imprinted on the CPR barrier device to reflect that the rescuer should position the nose tent of the CPR barrier device over the nose of the patient. Further, these instructions may show the rescuer what procedures he/she is supposed to follow during the administration of CPR. In FIG. 24, for example, instruction 110e shows that the rescuer should force the nose grip elements 23a and 23b inwardly to close the nostril airways of the patient.

Figure 25:
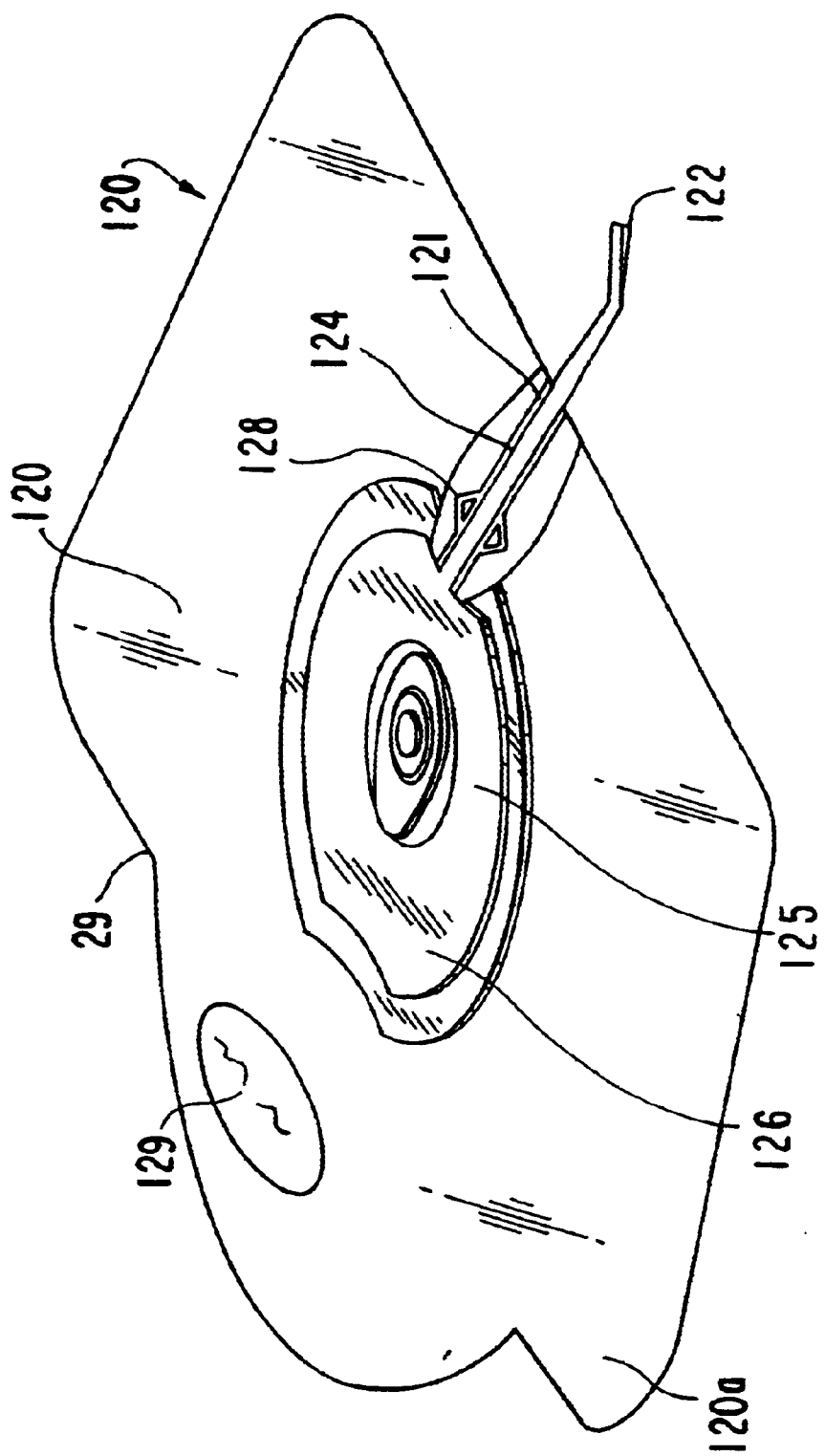
FIG. 25 is a top view of another preferred embodiment of a CPR barrier device in accordance with the teachings of the present invention.
Figure 26:
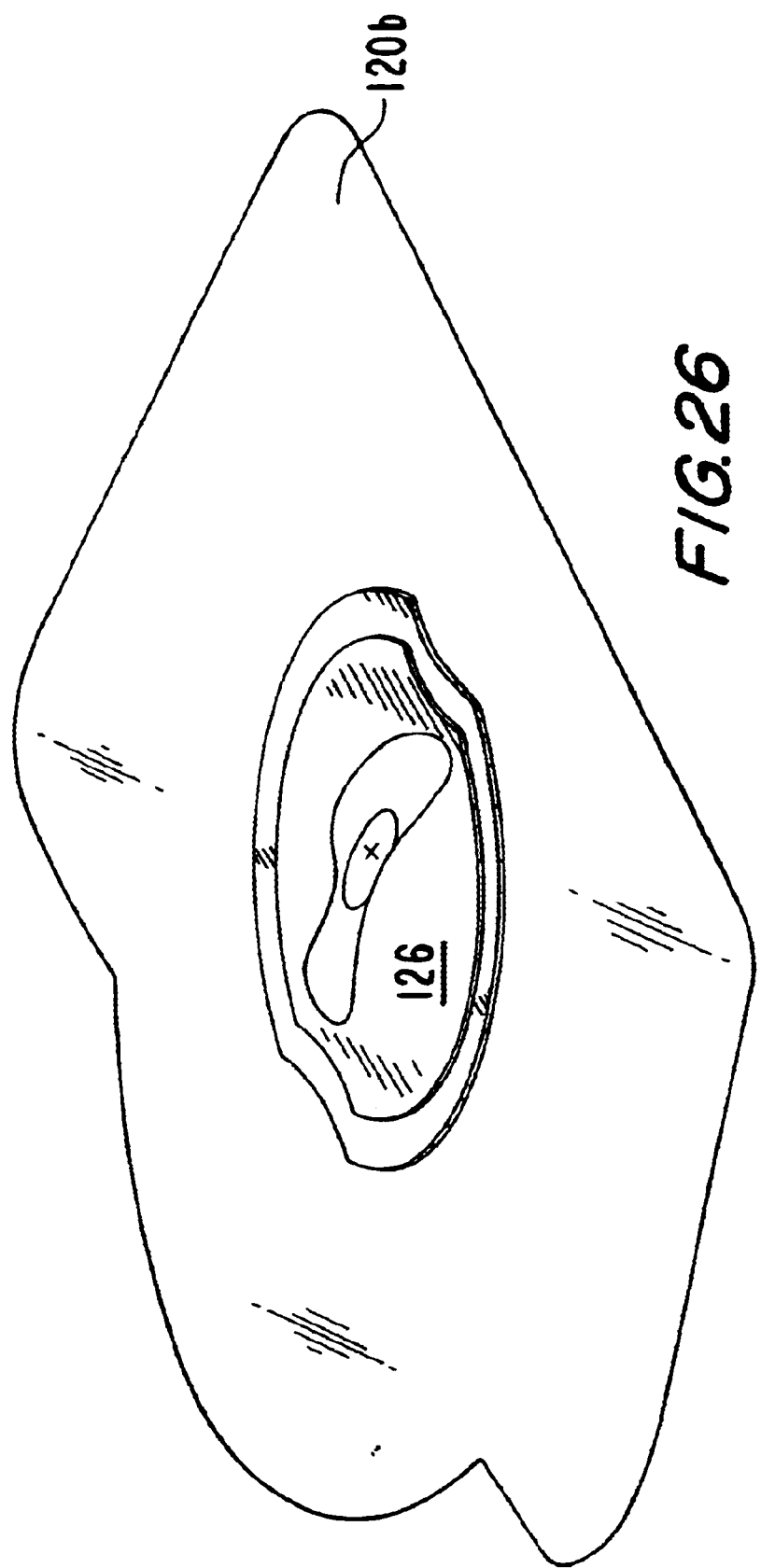
FIG. 26 is a bottom view of the CPR barrier device of FIG. 25.

FIGS. 25 and 26 illustrate another preferred embodiment of a CPR barrier device 120 in accordance with the teachings of the present invention. In this embodiment the inflation member 121 includes a blow tube member 122 which is capable of extending through the channel 124 into the air chamber 125 for blowing air from the rescuer into the air chamber 125 to inflate the inflatable portion 126. When the blow tube member 122 is withdrawn from the channel after inflation of the inflatable portion 126, positive pressure in the sealing member 128 of the inflatable portion closes the channel, thus sealing off the air chamber 125 to prevent air from escaping therefrom.

The process of manufacturing the inflation member 120 of FIGS. 25 and 26 will now be described. During this manufacturing process, one sheet 120a of the plastic film or membrane is thermally formed to render a "donut" shaped bulging detail in the film's surface. The second sheet 120b of plastic film or membrane is heat sealed over the first, closing over the "doughnut" detail, thus forming the air chamber 125 of entrapped air. During this process, the channel 124 formed of a flat tube of similar material is inserted between the two sheets of plastic film 120a and 120b communicating between the "donut" cavity and the outside of the barrier device. The end of this channel 124 extends approximately one-half inch into the "donut" cavity. Air is supplied through the blow tube member 122 inserted into the channel by the rescuer and is then withdrawn. The positive pressure inside the "doughnut" closes down the flat channel at the sealing member 128, thus sealing off the interior from the outside. The blow tube member 122 can also be used in manufacturing to deflate the "doughnut" in preparation for packaging.

As shown in FIG. 25, proper orientation of the CPR barrier device on the face of the patient can also be achieved by means of a forehead attachment member 129. This attachment member 129 can be in the form of a die cut head strap which is incorporated in the plastic membrane sheets. This head strap can alternately include an adhesive patch with a peel-away liner which attaches to the patient's forehead. In addition, die cut ear slits could as well be incorporated into the device's membrane sheets whereby the patient's ears can be inserted through the slits to further secure the device to the patient.

Figures 27, 28:
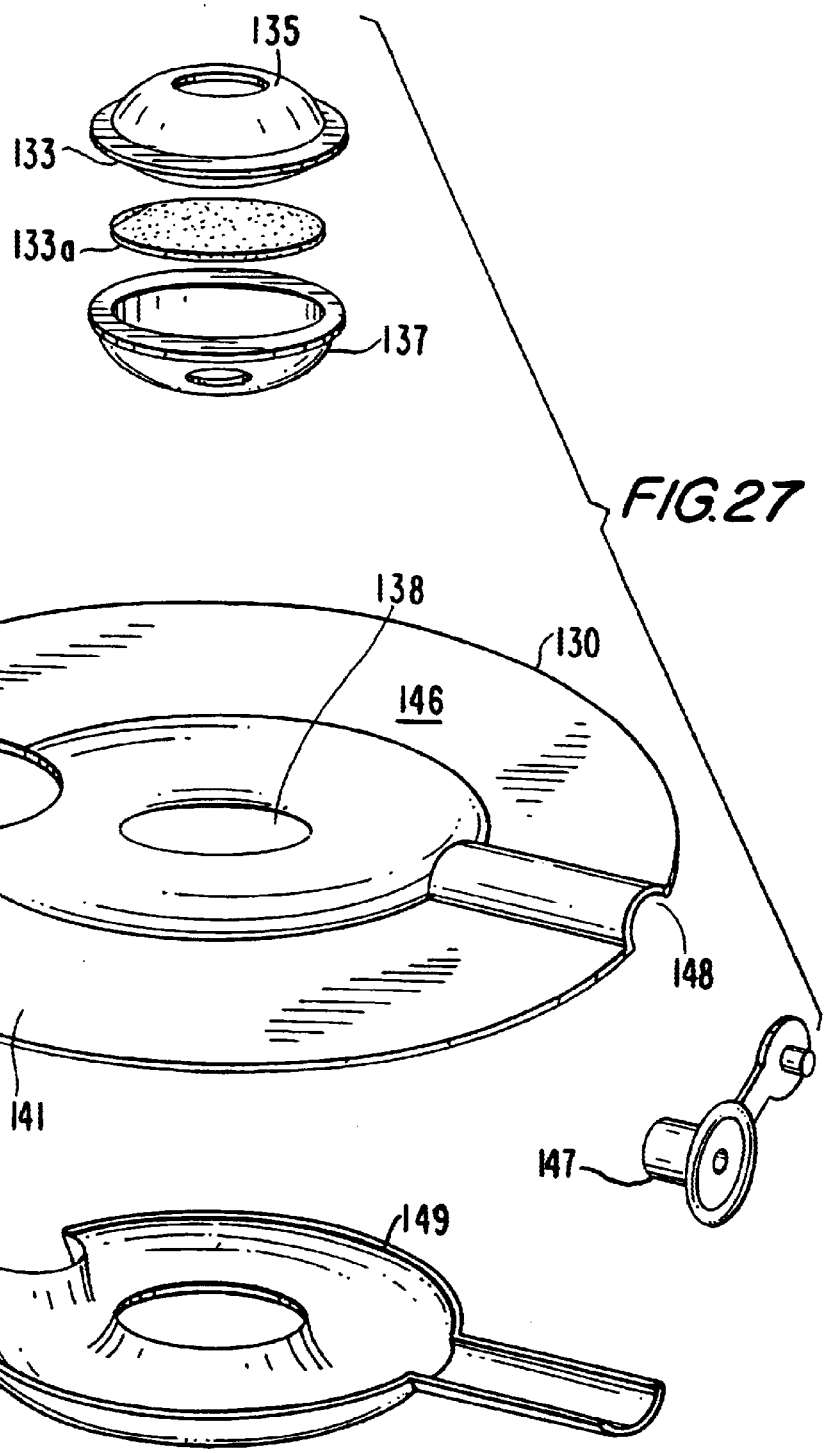
FIG. 27 is top exploded perspective view of another preferred embodiment of a CPR barrier device in accordance with the teachings of the present invention.
FIG. 28 is a top view of the bottom cuff of the CPR barrier device of FIG. 27.

Another embodiment for a CPR barrier device 130 in accordance with the teachings of the present invention is shown in FIGS. 27–28 of this application. As is shown therein, a filter assembly 133 is formed of a filter retainment housing 134 including a upper casing half 135 and a lower casing half 137 which enclose a filter 133a. This filter assembly 133 is contained within the central opening 138 of the barrier device 130. In addition, a nose accommodating hole 142 is provided in the top and bottom plastic sheets of the barrier device 130 such that the barrier device can be properly oriented on the patient. In addition, the nose accommodating hole 142 allows the flange 144 to be part of the top cuff housing 146. Therefore the flange 144 is capable of expanding or contracting. Moreover, an inflation fitment 147 can be fitted within the lateral openings 148a and 148b of the respective top cuff half 146 and bottom cuff half 149 to retain air within the inflatable portion of the barrier device of FIGS. 27 and 28.

Figure 32B:
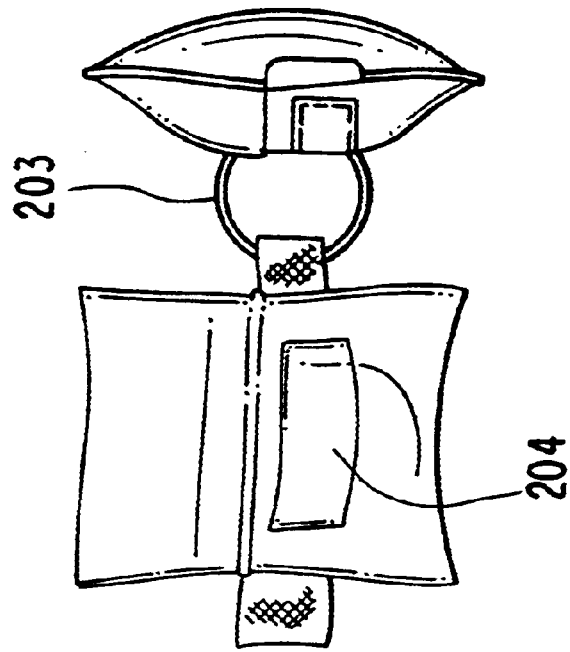
FIGS. 32a and 32b are views illustrating a preferred embodiment of a pouch for containing a CPR barrier device of the present invention.
Figure 32A:
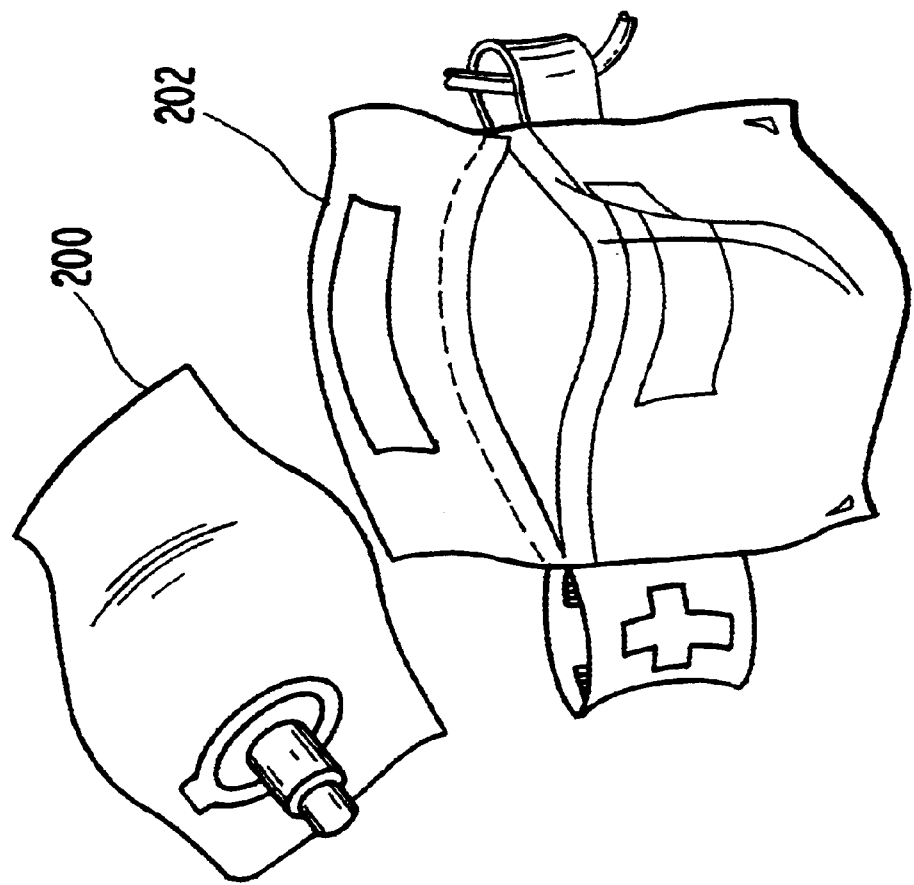
Figure 33:
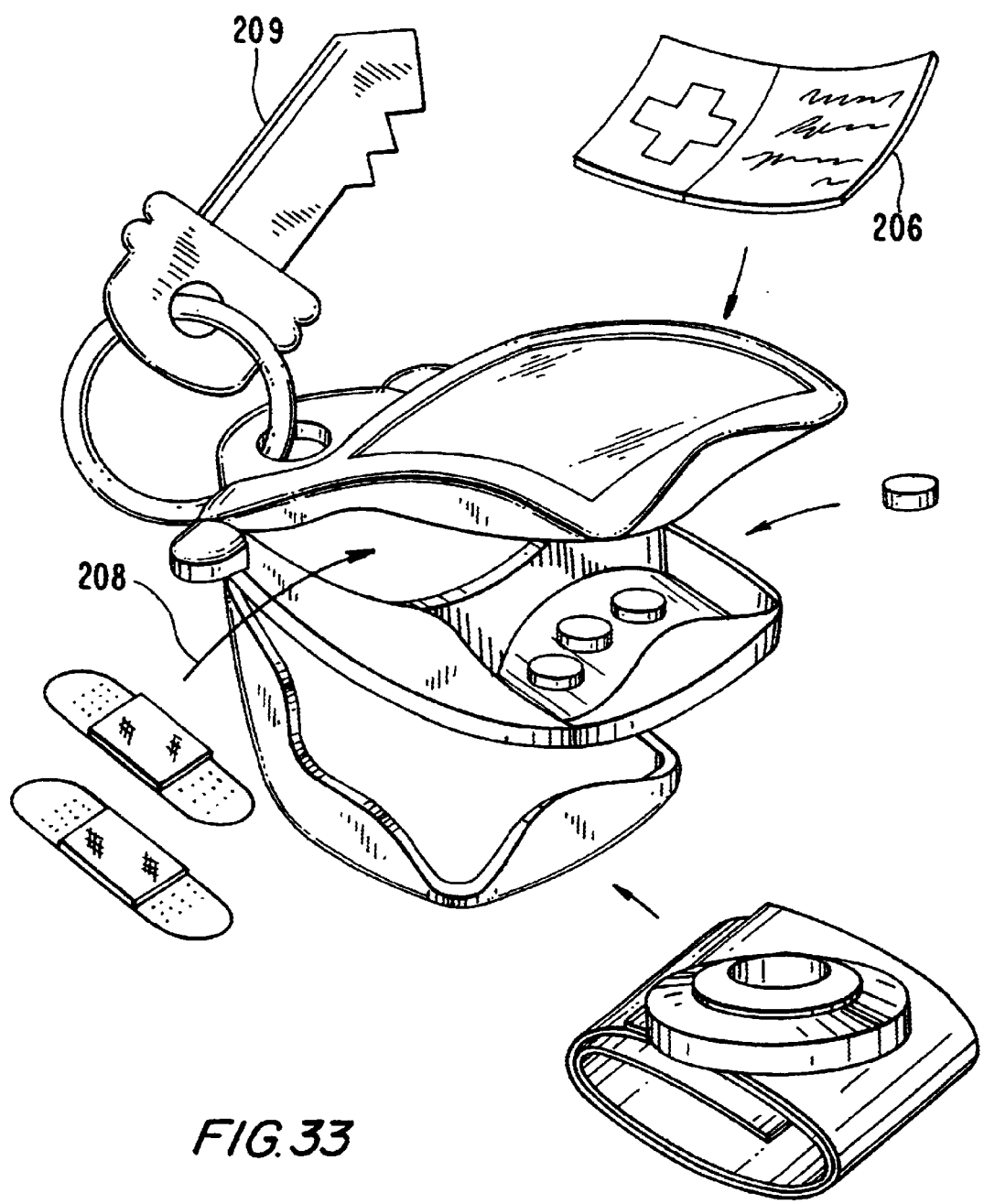
FIG. 33 is a front exploded perspective view of another preferred embodiment for a supply kit containing a CPR barrier device of the present invention.
Figure 34C:
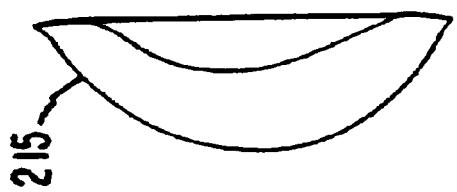
FIGS. 34a, 34b and 34c are views illustrating another preferred embodiment of a hard case for containing a CPR barrier device of the present invention.
Figure 34B:
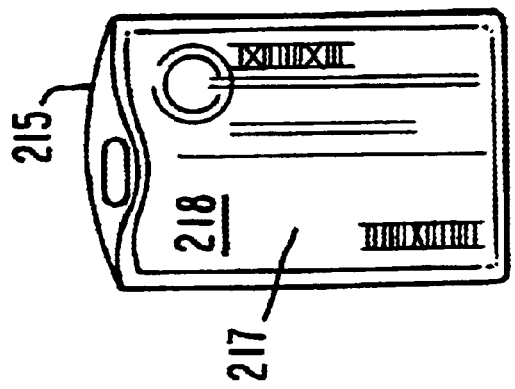
Figure 34A:
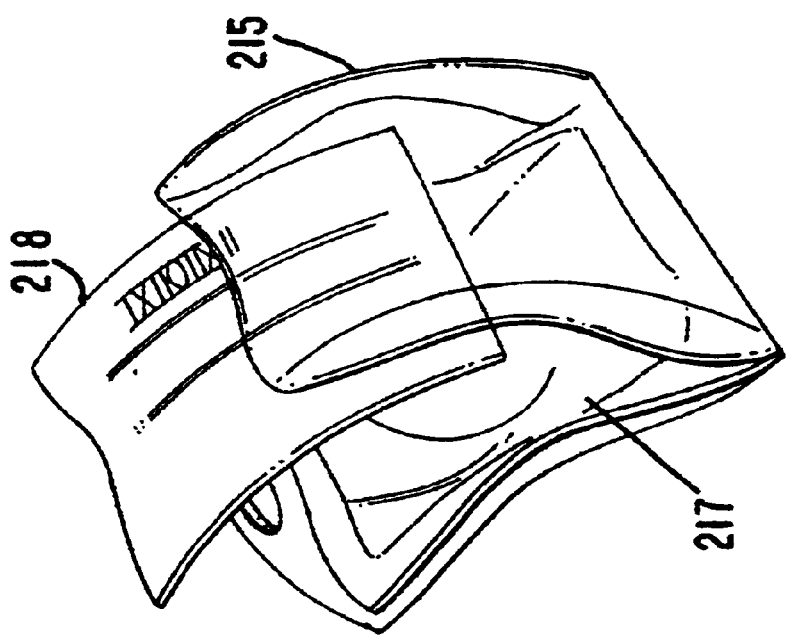
Figure 35C:
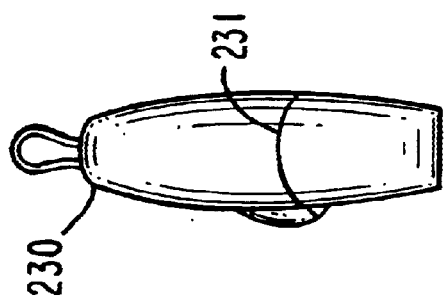
FIGS. 35a, 35b and 35c are views illustrating another preferred embodiment of a hard case for carrying a CPR barrier device of the present invention.
Figure 35B:
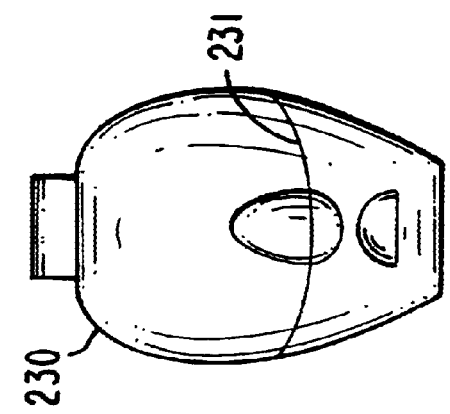
Figure 35A:
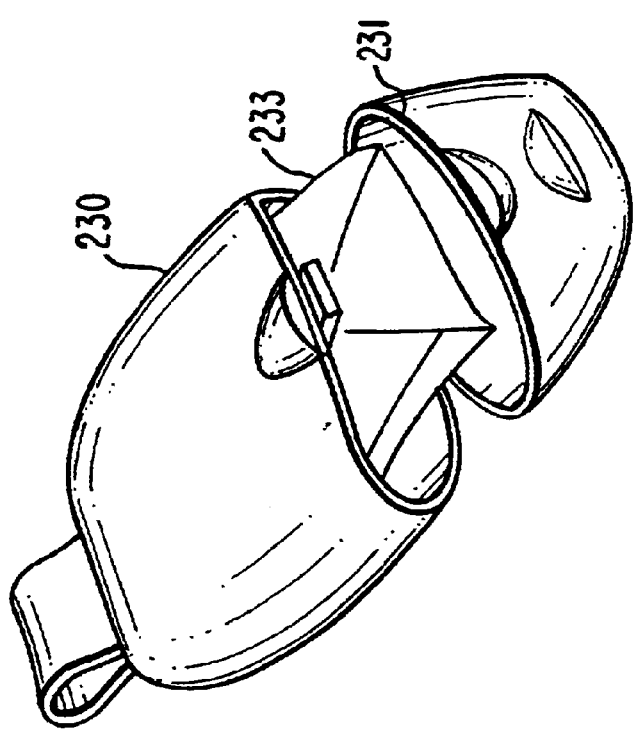
Figure 36C:
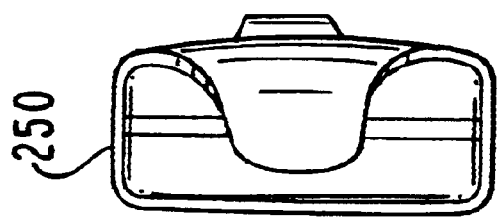
FIGS. 36a, 36b and 36c are views illustrating another preferred embodiment of a container for carrying the CPR barrier device of the present invention.
Figure 36B:
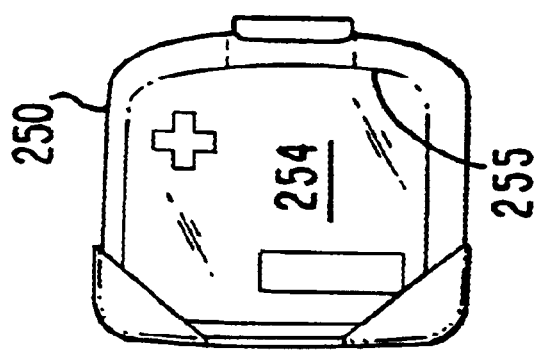
Figure 36A:
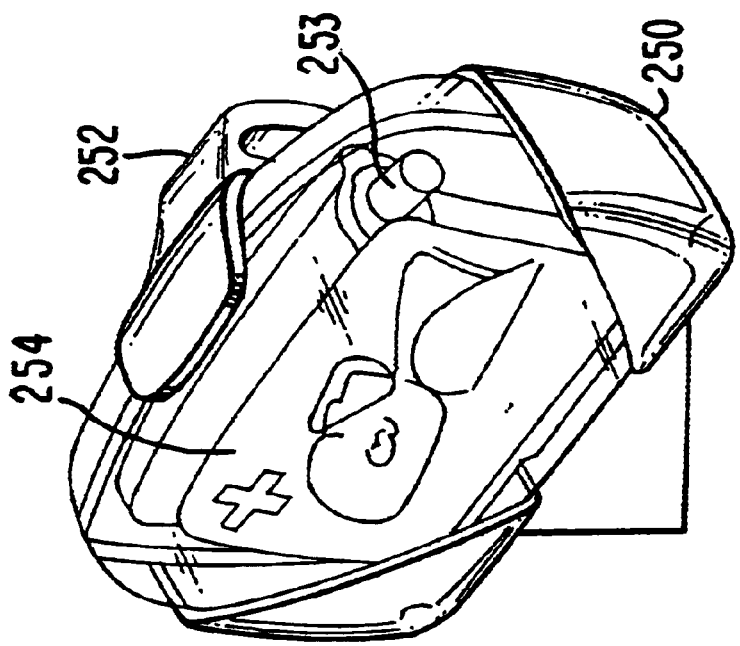
Figure 37C:
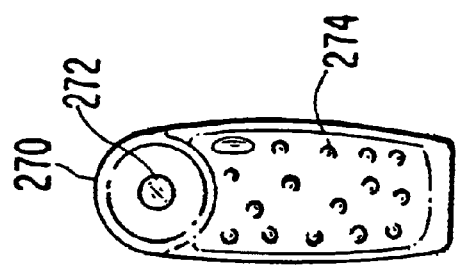
FIGS. 37a, 37b and 37c are views illustrating a hard case for carrying a CPR barrier device of the present invention.
Figure 37B:
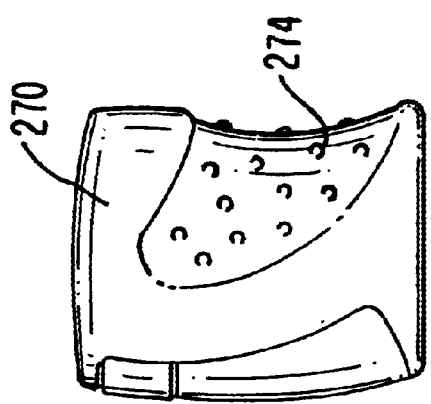
Figure 37A:
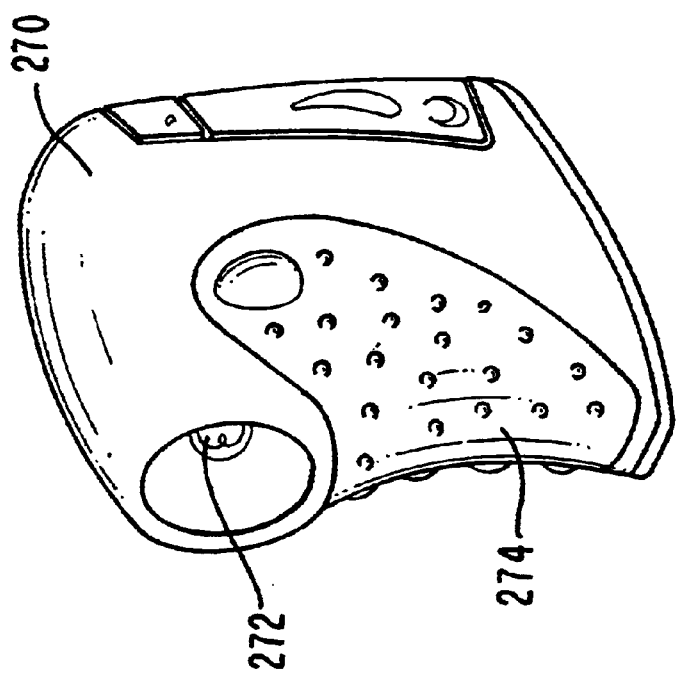

In addition, the shape and size of the CPR barrier device of the present invention has been optimized to be as small as possible. Thus, the packages and cases set forth below have likewise been designed to assist in this desired miniaturization. Moreover, the packages have been designed such that the inflation member such as the blow tube member is presented when the rescuer takes the CPR barrier device out of its packaging so that the CPR barrier device can be readily deflated. In accordance therewith, in FIGS. 32a and 32b, the CPR barrier device 200 is contained within a soft pouch 202 with key ring 203 in neoprene or nylon with velcro closing 204. In FIG. 33, an emergency supply kit 208 is provided with a key ring 209 that holds emergency supplies, certification card, etc. and a CPR barrier device of the present invention. FIGS. 34a, 34b and 34c illustrate a wallet style hard case 215 wherein the CPR barrier device 216 and instruction card 218 are visible through a transparent front face 217 thereof. FIGS. 35a, 35b and 35c illustrate a hard case 230 with hinged opening 231 which contains an integrated whistle 233 and CPR barrier device. FIGS. 36a, 36b and 36c illustrate a beeper style case 250 with belt attachment 252 that holds a CPR barrier 253 and certification card 254, etc. which can be seen through a transparent front face 255. FIGS. 37a, 37b and 37c illustrate a hard case 270 with integrated flashlight 272 with the CPR barrier device and instructions contained in a soft rubber grip compartment 274 of the flashlight.

Accordingly, in accordance with the general objects of the present invention, a CPR barrier device has been provided wherein airflow is communicated in the direction of the rescuer to the patient, but the patient's exhalation and bodily fluids are prevented from reaching the rescuer. In addition, this CPR barrier device prevents direct facial contact with a patient. Further, a nose pinch element can be provided in this CPR barrier device which assists the rescuer in sealing the nose of the patient and provides a cushioning effect when force is applied to the nose of the patient. Also, in order to assist the rescuer, this CPR barrier device includes orienting means for properly orienting the resuscitation device on the face of the patient. Moreover, the CPR barrier device can be rapidly and easily deployed by the rescuer and can be packaged in a variety of small carrier cases.

Although the invention has been particularly shown and described with reference to certain preferred embodiments, it will readily be appreciated by those of ordinary skill in the art that various changes and modifications may be made therein without departing from the spirit and scope of the invention. For instance, other techniques may be utilized to inflate the inflatable portion 12 other than those set forth herein. These include (1) generating a chemical reaction to fill the air chamber with gas; (2) utilizing a pump operated by fingers to inflate the air chamber; and (3) utilizing hollow capsules filled with pressurized air that, when fractured, fill the chamber with air. In addition, the CPR barrier device described above includes a filter which is incorporated in the ventilation/exhalation valve assembly. However, the present invention also contemplates that a ventilation/exhalation valve member could be incorporated in the CPR barrier device of the present invention which does not include a filter.

Figure 38A:
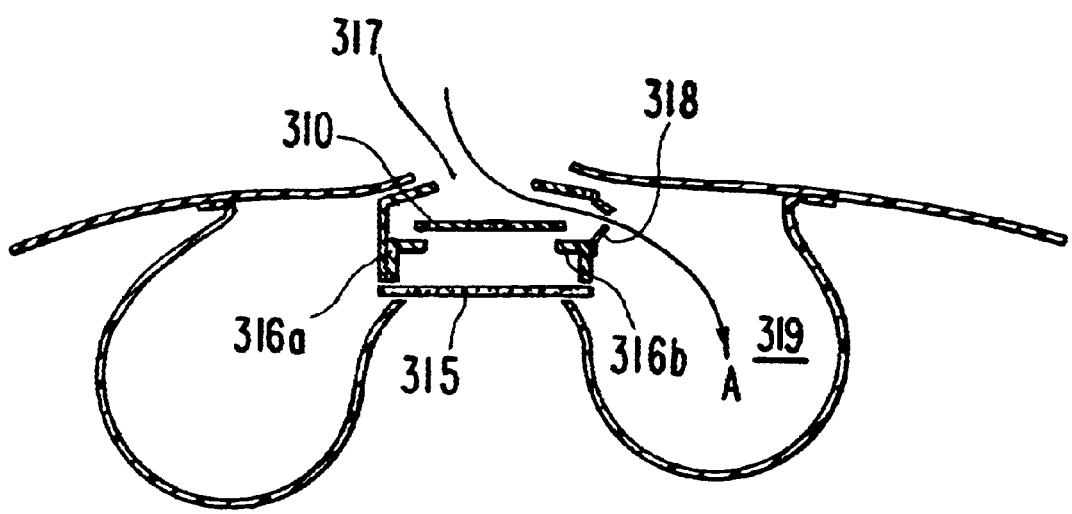
FIG. 38a is a side section view of a first preferred technique for inflating the inflatable portion through the patient valve assembly with a pneumatic switch in a first position.
Figure 38B:
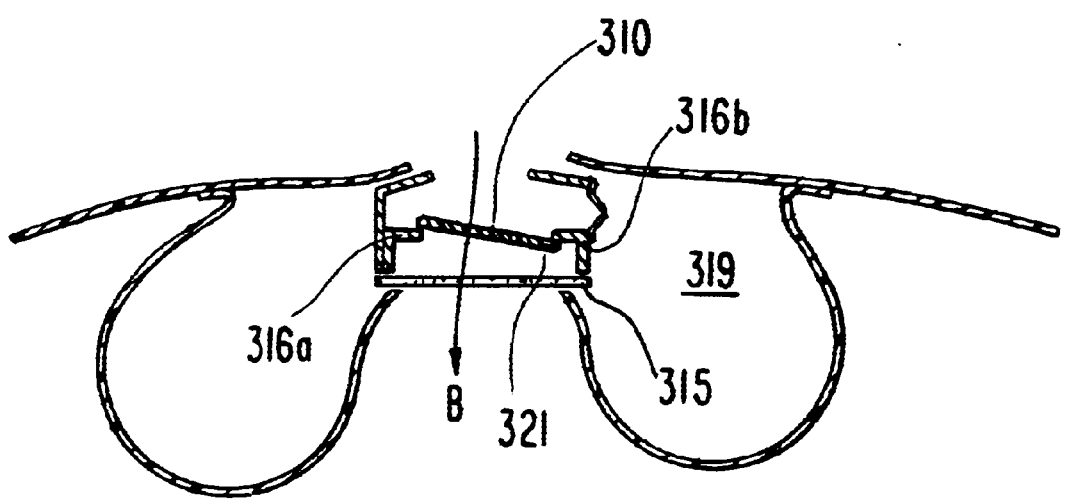
FIG. 38b is a side sectional view of the technique for inflating the inflatable portion through the patient valve assembly of FIG. 38a with the pneumatic switch in a second position.

In addition, the present invention also contemplates that the inflation of the inflatable portion occurs through the ventilation/exhalation valve assembly. Examples of such inflation techniques are shown in FIGS. 38a–b and 39a–b herein. In the embodiment of FIGS. 38a–b, a pneumatic switch 310 is provided in the ventilation/exhalation valve assembly 315. As shown in FIG. 38a, in its first position, the pneumatic switch 310 is set in a generally horizontal position on flange members 316a and b of the valve assembly 315 so that the rescuer's air entering valve opening 317 is diverted by the pneumatic switch 310 through valve flap opening 318 to inflate the inflatable portion 319 in the direction of arrow A. When sufficient pressure is achieved within the inflatable portion 319, the valve flap opening 318 closes and the pneumatic switch 310 is deflected at an end 321 thereof to a second and final position removed from the flange member 316b such that the patient can be ventilated in the direction of arrow B (see FIG. 38b).

Figure 39A:
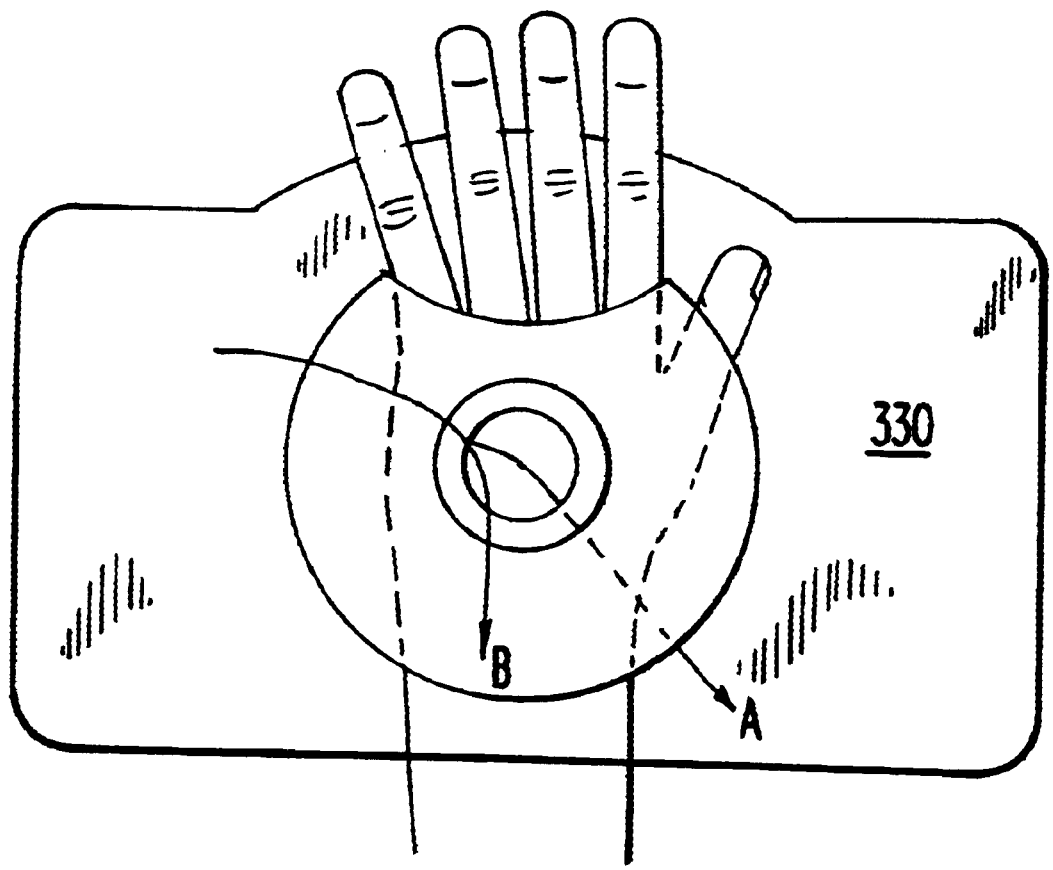
FIG. 39a is a top plan view showing another technique for inflating the inflatable portion through the patient valve assembly by means of using the rescuer's hand to occlude the patient valve assembly to allow initial inflation of the inflatable portion.
Figure 39B:
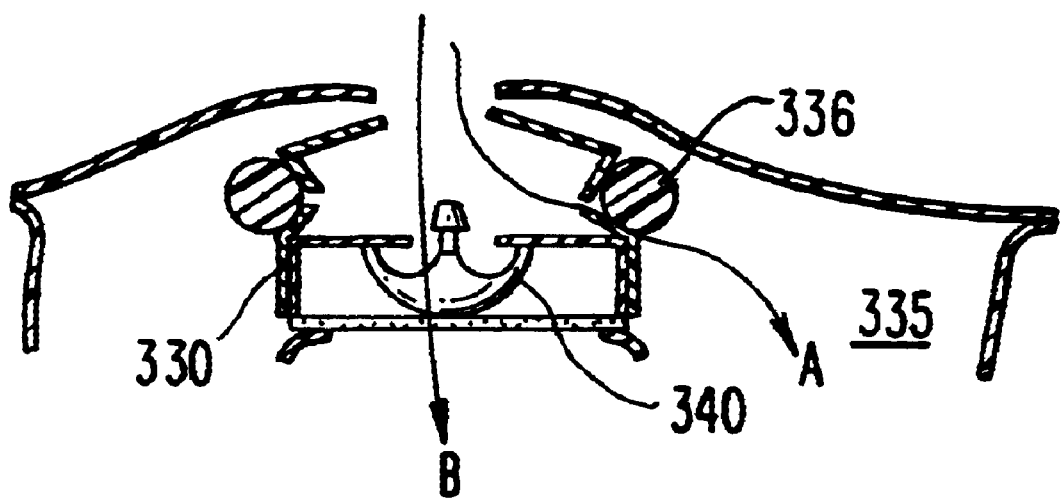

In the inflation technique of FIGS. 39a–b, the rescuer's hand occludes the patient valve 330 to allow initial inflation of the inflatable portion 335 through the flap openings 336 in the direction of arrow A. When sufficient pressure is reached within the inflatable portion 335 and the rescuer's hand is removed from its occluding position, the flap openings 336 are closed and the rescuer's air passes through the patient valve 330 in the direction of arrow B to ventilate the patient. As shown in FIG. 39b, a one-way valve 340 is provided in the patient valve 330 allowing ventilated air to pass to the patient and preventing exhaled air and bodily fluids of the patient reaching the rescuer.

It is intended that the appended claims be interpreted as including the foregoing as well as various other such changes and modifications.

What is claimed is:

1. A resuscitation device for providing a barrier between a rescuer and a patient requiring mouth-to-mouth resuscitation comprising:
    an inflatable portion which when inflated extends in the breathing direction between the rescuer and the patient so that an outer perimetral portion thereof is placed around at least one breathing organ of the patient;
    inflation means for inflating said inflatable portion;
    first valve means for permitting airflow from the rescuer to the patient and for preventing the exhalation and the bodily fluids of the patient from reaching the rescuer; and
    barrier means for shielding the rescuer from the patient, said barrier means extending outwardly from said outer perirnetral portion of said inflatable portion.

2. The resuscitation device of claim 1 wherein said inflatable portion is formed of two sheets of flexible film to form an air chamber therebetween.

3. The resuscitation device of claim 2 wherein said air chamber when inflated forms a pillow-like member to be placed around the at least one breathing organ of the patient.

4. The resuscitation device of claim 2 wherein said inflation means includes second valve means for sealing said air chamber in its inflated condition.

5. The resuscitation device of claim 4 wherein said second valve means includes channel means for providing a conduit between said second valve means and said air chamber.

6. The resuscitation device of claim 5 wherein said channel means includes sealing means for providing an airtight seal to retain said inflatable portion in its said inflated condition and thereby prevent leakage of air from said inflatable portion.

7. The resuscitation device of claim 4 wherein said inflation means includes blowing means capable of extending through said channel means into said air chamber for blowing air from the rescuer into said air chamber to inflate said inflatable portion.

8. The resuscitation device of claim 7 wherein said blowing means is a tube member.

9. The resuscitation device of claim 4 wherein second valve means includes valve closing means which prevents air from escaping from said air chamber is inflated.

10. The resuscitation device of claim 9 wherein said valve closing means includes a pair of flexible flap members which close a valve opening to said air chamber upon sufficient back pressure in said air chamber.

11. The resuscitation device of claim 1 wherein said inflatable portion includes nostril closing assist means for assistance in pinching the nostrils of the patient to close the same.

12. The resuscitation device of claim 11 wherein said nostril closing assist means includes inflatable nose pinch elements which close inwardly upon the nostrils of the patient when the inflatable portion is inflated to assist the rescuer in restricting airflow through the nostrils.

13. The resuscitation device of claim 12 and further including positioning assist means for properly orienting the resuscitation device on the face of the patient.

14. The resuscitation device of claim 13 wherein said positioning means includes a tented portion provided between said nose pinch elements to cover the nose of the patient to properly orient the resuscitation device on the face of the patient.

15. The resuscitation device of claim 1 wherein said first valve means includes filter means for filtering fluid or foreign materials exhaled from the patient.

16. The resuscitation device of claim 15 wherein said filter means is made of a substantially opaque, porous material.

17. The resuscitation device of claim 15 wherein said filter means is secured to said first valve means by means of a filter retaining ring.

18. The resuscitation device of claim 1 wherein said first valve means includes a top housing and a bottom housing secured to one another.

19. The resuscitation device of claim 1 wherein said first valve means includes a flexible valve member for allowing air to flow from the rescuer to the patient but prevents exhalation and bodily fluids of the patient from reaching the rescuer.

20. The resuscitation device of claim 19 wherein said flexible valve member is a flexible diaphragm which is movable between a flexed condition, wherein ventilation from the rescuer to the patient is permitted, and an unflexed condition, wherein the exhalation and bodily fluids of the patient is blocked from reaching the rescuer.

21. The resuscitation device of claim 20 wherein in said unflexed condition of said flexible diaphragm, the exhalation of the patient is diverted through an exhalation diversion opening provided in said first valve means.

22. The resuscitation device of claim 21 wherein said first valve means includes covering means surrounding said exhalation diversion opening to shield the diverted patient exhalation from the rescuer.

23. The resuscitation device of claim 1 wherein said barrier means is flexibly attached to said inflatable portion.

24. The resuscitation device of claim 23 wherein said barrier means includes attachment means for attaching the resuscitation device to a body portion of the patient.

25. The resuscitation device of claim 1 wherein said inflation means extends generally perpendicular to the direction of exhalation of the patient.

26. A resuscitation device for providing a barrier between a rescuer and a patient requiring mouth-to-mouth resuscitation comprising:
    an inflatable portion which when inflated extends in the breathing direction between the rescuer and the patient so as to be placed around at least one breathing organ of the patient, said inflatable portion having a generally centrally located opening therein; and first valve means provided in said opening of said inflatable portion for permitting airflow from the rescuer to the patient and for preventing exhalation and bodily fluids of the patient from reaching the rescuer with said exhalation and bodily fluids of the patient being exhausted through openings provided in said first valve means.

27. The resuscitation device of claim 26 wherein said inflatable portion is formed of two sheets of flexible film to form an air chamber therebetween.

28. The resuscitation device of claim 27 wherein said air chamber when inflated forms a pillow-like member to be placed around the at least one breathing organ of the patient.

29. The resuscitation device of claim 26 wherein said inflatable portion includes nostril closing assist means for assistance in pinching the nostrils of the patient to close the same.

30. The resuscitation device of claim 29 wherein said nostril closing assist means includes inflatable nose pinch elements which extend inwardly so as to be in a position to pinch the nostrils of the patient when the inflatable portion is inflated to assist the rescuer in restricting air flow through the nostrils.

31. The resuscitation device of claim 30 and further including positioning means for properly orienting the resuscitation device on the face of the patient.

32. The resuscitation device of claim 31 wherein said positioning means includes a tented portion provided between said nose pinch elements to cover the nose of the patient to properly orient the resuscitation device on the face of the patient.

33. The resuscitation device of claim 26 wherein said first valve means includes filter means for permitting air to flow from the rescuer to the patient and for filtering exhalation or bodily fluids of the patient.

34. The resuscitation device of claim 33 wherein said filter means is made of a substantially opaque, porous material.

35. The resuscitation device of claim 26 wherein said first valve means includes a flexible diaphragm which is movable between a flexed condition, wherein ventilation from said rescuer is permitted to pass through said first valve means into the breathing organ of the patient, and an unflexed condition, wherein exhalation and bodily fluids of the patient is blocked from reaching the rescuer.

36. The resuscitation device of claim 35 wherein in said unflexed condition of said flexible diaphragm, the exhalation and bodily fluids of the patient are diverted through an exhalation diversion opening provided in said first valve means.

37. The resuscitation device of claim 36 wherein said first valve means includes covering means surrounding said exhalation diversion opening to shield the diverted patient exhalation and bodily fluids from the rescuer.

38. The resuscitation device of claim 26 wherein said first valve means has a contoured mouthpiece.

39. The resuscitation device of claim 26 and further including inflation means for inflating said inflatable portion which includes air receiving means for receiving airflow from the rescuer to inflate said inflatable portion.

40. The resuscitation device of claim 39 wherein inflation means further includes second valve means which permits air to be received into said air chamber of said inflatable portion and prevents air from escaping from said air chamber when in its inflated condition.

41. The resuscitation device of claim 40 wherein said second valve means includes valve sealing means for providing an airtight seal to retain said inflatable portion in its said inflated condition and thereby prevent leakage of air from said inflatable portion.

42. The resuscitation device of claim 41 wherein said valve sealing means includes a pair of flexible flap members which close a valve opening to said air chamber upon sufficient back pressure created in said air chamber.

43. The resuscitation device of claim 40 wherein said second valve means includes means for releasing the pressure in said inflatable portion.

44. The resuscitation device of claim 26 and further comprising positioning assist means for properly orienting the resuscitation device on the face of the patient.

45. The resuscitation device of claim 44 wherein said positioning assist means includes a relief portion to conform to the nose of the patient to properly orient the resuscitation device on the patient.

46. The resuscitation device of claim 26 wherein said inflation means extends generally perpendicular to the direction of the exhalation of the patient.

47. The resuscitation device of claim 26 and further comprising barrier means for shielding the rescuer from the patient.

48. The resuscitation device of claim 47 wherein said barrier means is flexibly attached to said inflatable portion.

49. The resuscitation device of claim 47 wherein said barrier means is wider at a chin portion thereof than at a nose portion thereof.

50. The resuscitation device of claim 47 wherein said barrier means includes attachment means for attaching the resuscitation device to a body portion of the patient.

51. A resuscitation device for providing a barrier between a rescuer and a patient requiring mouth-to-mouth resuscitation comprising:
a ventilation/exhalation valve assembly for permitting airflow from the rescuer to the patient and for preventing exhalation and bodily fluids of the patient from reaching the rescuer, said valve assembly including a flexible diaphragm which is movable between a flexed condition, wherein ventilation from said rescuer is permitted to pass through said valve assembly into a breathing organ of the patient, and an unflexed condition, wherein exhalation and bodily fluids of the patient are blocked from reaching the rescuer and are exhausted through openings provided in said ventilation/exhalation valve assenibly.

52. The resuscitation device of claim 51 wherein said ventilation/exhalation valve assembly includes an exhalation diversion opening formed therein through which the exhalation and bodily fluids of the patient are diverted when the exhalation and bodily fluids of the patient are blocked by the flexible diaphragm when the flexible diaphragm is in its unflexed condition.

53. The resuscitation device of claim 52 wherein said ventilation/exhalation valve assembly includes covering means surrounding said exhalation diversion opening to shield the diverted patient exhalation and bodily fluids from the rescuer.

54. The resuscitation device of claim 53 wherein said covering means is in the form of a downwardly depending inverted U-shaped extension surrounding said exhalation diversion opening.

55. The resuscitation device of claim 51 wherein said ventilation/exhalation valve assembly is formed of an upper housing and a lower housing which are sealed with respect to each other by means of a projecting edge extending from said upper housing to close a gap formed between the upper and lower housings.

56. The resuscitation device of claim 51 wherein said ventilation/exhalation valve assembly includes an upper housing and a lower housing which are secured to one another.

57. The resuscitation device of claim 56 wherein said upper housing includes a plurality of downwardly depending legs which are engaged in respective spaced recesses provided along an inner circumferential surface of said lower housing to secure the upper housing to the lower housing.

58. The resuscitation device of claim 56 and further including means for supporting said flexible diaphragm within said ventilation/exhalation valve assembly.

59. The resuscitation device of claim 58 wherein said supporting means includes a circumferential flange depending downwardly from said upper housing which abuts against an upper surface of said flexible diaphragm to restrict upward movement of said flexible diaphragm when said flexible diaphragm in its unflexed condition.

60. The resuscitation device of claim 58 wherein said supporting means includes a diaphragm support and flexing assembly extending inwardly from a main cylindrical body of said lower housing.

61. The resuscitation device of claim 60 wherein said diaphragm support and flexing assembly includes peripheral confining means for aligning and confining an outer peripheral surface of the flexible diaphragm within said ventilation/exhalation valve member.

62. The resuscitation device of claim 61 wherein said peripheral confining means includes an arcuate rim section extending from said support and flexing assembly which confines and abuts the outer peripheral surface of said flexible diaphragm.

63. The resuscitation device of claim 60 wherein said diaphragm support and flexing assembly includes an inclined ramp member extending upwardly from said diaphragm support and flexing assembly which abuts against a bottom surface of said flexible diaphragm so as to provide a fulcrum point so that the flexible diaphragm can be flexed downwardly during ventilation by the rescuer.

64. The resuscitation device of claim 60 wherein said diaphragm support and flexing assembly includes a generally semi-circular projection extending therefrom on which the bottom surface of said flexible diaphragm is supported.

65. The resuscitation device of claim 56 wherein said ventilation exhalation valve assembly includes filter means for filtering fluid or foreign materials exhaled from the patient.

66. The resuscitation device of claim 65 wherein said filter means is made of a substantially opaque, porous material.

67. The resuscitation device of claim 64 and further including a filter retaining ring for securing the filter to the ventilation/exhalation valve member.

68. The resuscitation device of claim 67 wherein said filter retaining ring is secured to said lower housing.

69. A resuscitation device for providing a barrier between a rescuer and a patient requiring mouth-to-mouth resuscitation comprising:
an inflatable portion which when inflated extends in the breathing direction between the rescuer and the patient so as to be placed around at least one breathing organ of the patient wherein said inflatable portion includes nostril closing assist means for pinching the nostrils of the patient to close the same.

70. The resuscitation device of claim 69 wherein said nostril closing assist means includes inflatable nose pinch elements which pinch the nostrils of the patient when the inflatable portion is inflated to assist the rescuer in restricting airflow through the nostrils.

71. A resuscitation device for providing a barrier between a rescuer and a patient requiring mouth-to-mouth resuscitation comprising:
an inflatable portion which when inflated extends in the breathing direction between the rescuer and the patient so that an outer perimetral portion thereof is placed around at least one breathing organ of the patient, said inflatable portion having a central opening therein;
inflation means for inflating said inflatable portion;
filter means provided in said central opening for filtering fluid or foreign materials from being passed between the patient and the rescuer; and
barrier means for shielding the rescuer from the patient, said barrier means extending outwardly from said outer perimetral portion of said inflatable portion.

72. The resuscitation device of claim 71 wherein said filter means is made of a substantially opaque, porous material.

73. A resuscitation device for providing a barrier between a rescuer and a patient requiring mouth-to-mouth resuscitation comprising:
an inflatable portion inflatable between an uninflated condition, wherein said inflatable portion is capable of lying generally flat around at least one breathing organ of the patient, and an inflated condition, wherein said inflatable portion is inflated in the breathing direction between the rescuer and the patient so as to be placed around at least one breathing organ of the patient;
inflation means for inflating said inflatable portion from its uninflated condition to its said inflated condition;
first valve means for permitting airflow from the rescuer to the patient and for preventing the exhalation and bodily fluids of the patient from reaching the rescuer;
barrier means for shielding the rescuer from the patient; and
wherein the resuscitation device permits mouth-to-mouth resuscitation to occur in both the uninflated and inflated conditions of said inflatable portion.

74. A resuscitation device for providing a barrier between a rescuer and a patient requiring mouth-to-mouth resuscitation comprising:
an inflatable portion which when inflated extends in the breathing direction between the rescuer and the patient so as to be placed around at least one breathing organ of the patient, said inflatable portion having a central opening therein;
inflation means for inflating said inflatable portion from its uninflated condition to its inflated condition;
filter means provided in said central opening for filtering fluid or foreign materials being passed between the patient and the rescuer;
barrier means for shielding the rescuer from the patient; and
wherein the resuscitation device permits mouth-to-mouth resuscitation to occur in both the uninflated and inflated condition of said inflatable portion.

75. A resuscitation device for providing a barrier between a rescuer and a patient requiring mount-to-mouth resuscitation comprising:
an inflatable portion which when inflated extends in the breathing direction between the rescuer and the patient so as to be placed around at least one breathing organ of the patient; and a ventilation/exhalation valve assembly for permitting airflow from the rescuer to the patient and for preventing exhalation and bodily fluids of the patient from reaching the rescuer as the exhalation and bodily fluids of the patient are exhausted through openings provided in the ventilation/exhalation valve assembly, said ventilation/exhalation valve assembly including inflation means for inflating said inflatable portion.

76. A resuscitation device for providing a barrier between a rescuer and a patient requiring mouth-to-mouth resuscitation comprising:

an inflatable portion which when inflated extends in the breathing direction between the rescuer and the patient so as to be placed around at least one breathing organ of the patient, wherein said inflatable portion includes nostril closing assist means for assistance in pinching the nostrils of the patient to close the same;

inflation means for inflating said inflatable portion;

first valve means for permitting airflow from the rescuer to the patient and for preventing the exhalation and the bodily fluids of the patient from reaching the rescuer; and barrier means for shielding the rescuer from the patient.

77. The resuscitation device of claim 76 wherein said nostril closing assist means includes inflatable nose pinch elements which close inwardly upon the nostrils of the patient when the inflatable portion is inflated to assist the rescuer in restricting airflow through the nostrils.

78. The resuscitation device of claim 77 and further including positioning assist means for properly orienting the resuscitation device on the face of the patient.

79. The resuscitation device of claim 78 wherein said positioning means includes a tented portion provided between said nose pinch elements to cover the nose of the patient to properly orient the resuscitation device on the face of the patient.

80. A resuscitation device for providing a barrier between a rescuer and a patient requiring mouth-to-mouth resuscitation comprising:

an inflatable portion which when inflated extends in the breathing direction between the rescuer and the patient so as to be placed around at least one breathing organ of the patient;

inflation means for inflating said inflatable portion;

first valve means for permitting airflow from the rescuer to the patient and for preventing the exhalation and the bodily fluids of the patient from reaching the rescuer, said first valve means including filter means for filtering fluid or foreign materials exhaled from the patient, said filter means being secured to said first valve means by means of a filter retaining ring; and barrier means for shielding the rescuer from the patient.

81. A resuscitation device for providing a barrier between a rescuer and a patient requiring mouth-to-mouth resuscitation comprising:

an inflatable portion which when inflated extends in the breathing direction between the rescuer and the patient so as to be placed around at least one breathing organ of the patient, said inflatable portion having a generally centrally located opening therein, said inflatable portion including nostril closing assist means for assistance in pinching the nostrils of the patient to close the same; and first valve means provided in said opening of said inflatable portion for permitting airflow from the rescuer to the patient and for preventing exhalation and bodily fluids of the patient from reaching the rescuer.

82. The resuscitation device of claim 81 wherein said nostril closing assist means includes inflatable nose pinch elements which extend inwardly so as to be in a position to pinch the nostrils of the patient when the inflatable portion is inflated to assist the rescuer in restricting air flow through the nostrils.

83. The resuscitation device of claim 82 and further including positioning means for properly orienting the resuscitation device on the face of the patient.

84. The resuscitation device of claim 83 wherein said positioning means includes a tented portion provided between said nose pinch elements to cover the nose of the patient to properly orient the resuscitation device on the face of the patient.

85. A resuscitation device for providing a barrier between a rescuer and a patient requiring mouth-to-mouth resuscitation comprising:

an inflatable portion which when inflated extends in the breathing direction between the rescuer and the patient so as to be placed around at least one breathing organ of the patient said inflatable portion having a generally centrally located opening therein;

inflation means for inflating said inflatable portion which includes air receiving means for receiving airflow from the rescuer to inflate said inflatable portion; and first valve means provided in said opening of said inflatable portion for permitting airflow from the rescuer to the patient and for preventing exhalation and bodily fluids of the patient from reaching the rescuer.

86. The resuscitation device of claim 85 wherein said inflation means further includes second valve means which permits air to be received into said air chamber of said inflatable portion and prevents air from escaping from said air chamber when in its inflated condition.

87. The resuscitation device of claim 86 wherein said second valve means includes valve sealing means for providing an airtight seal to retain said inflatable portion in its said inflated condition and thereby prevent leakage of air from said inflatable portion.

88. The resuscitation device ofclaim 87 wherein said valve sealing means includes a pair of flexible flap members which close a valve opening to said air chamber upon sufficient back pressure created in said air chamber.

89. The resuscitation device of claim 86 wherein said second valve means includes means for releasing the pressure in said inflatable portion.

90. A resuscitation device for providing a barrier between a rescuer and a patient requiring mouth-to-mouth resuscitation comprising:

an inflatable portion which when inflated extends in the breathing direction between the rescuer and the patient so as to be placed around at least one breathing organ of the patient said inflatable portion having a generally centrally located opening therein;

first valve means provided in said opening of said inflatable portion for permitting airflow from the rescuer to the patient and for preventing exhalation and bodily fluids of the patient from reaching the rescuer; and positioning assist means for properly orienting the resuscitation device on the face of the patient.

91. The resuscitation device of claim 90 wherein said inflation means extends generally perpendicular to the direction of the exhalation of the patient.

92. A resuscitation device for providing a barrier between a rescuer and a patient requiring mouth-to-mouth resuscitation comprising:

a ventilation/exhalation valve assembly for permitting airflow from the rescuer to the patient and for preventing exhalation and bodily fluids of the patient from reaching the rescuer, said valve assembly including a flexible diaphragm which is movable between a flexed condition, wherein ventilation from said rescuer is permitted to pass through said valve assembly into a breathing organ of the patient, and an unflexed condition, wherein exhalation and bodily fluids of the patient are blocked from reaching the rescuer, said ventilation/exhalation valve assembly including an exhalation diversion opening formed therein through which the exhalation and bodily fluids of the patient are diverted when the exhalation and bodily fluids of the patient are blocked by the flexible diaphragm when the flexible diaphragm is in its unflexed condition, said ventilation/exhalation valve assembly further including covering means surrounding said exhalation diversion opening to shield the diverted patient exhalation and bodily fluids from the rescuer, wherein said covering means is in the form of a downwardly depending inverted U-shaped extension surrounding said exhalation diversion opening.

93. A resuscitation device for providing a barrier between a rescuer and a patient requiring mouth-to-mouth resuscitation comprising:

a ventilation/exhalation valve assembly for permitting airflow from the rescuer to the patient and for preventing exhalation and bodily fluids of the patient from reaching the rescuer, said valve assembly including a flexible diaphragm which is movable between a flexed condition, wherein ventilation from said rescuer is permitted to pass through said valve assembly into a breathing organ of the patient, and an unflexed condition, wherein exhalation and bodily fluids of the patient are blocked from reaching the rescuer, said ventilation/exhalation assembly including an upper housing and a lower housing which are secured to one another, said upper housing including a plurality of downwardly depending legs which are engaged in respective spaced recesses provided along an inner circumferential surface of said lower housing to secure the upper housing to the lower housing.

94. A resuscitation device for providing a barrier between a rescuer and a patient requiring mouth-to-mouth resuscitation comprising:

a ventilation/exhalation valve assembly for permitting airflow from the rescuer to the patient and for preventing exhalation and bodily fluids of the patient from reaching the rescuer, said valve assembly including a flexible diaphragm which is movable between a flexed condition, wherein ventilation from said rescuer is permitted to pass through said valve assembly into a breathing organ of the patient, and an unflexed condition, wherein exhalation and bodily fluids of the patient are blocked from reaching the rescuer, said ventilation/exhalation assembly including an upper housing and a lower housing which are secured to one another; and means for supporting said flexible diaphragm within said ventilation/exhalation valve assembly, said supporting means including a diaphragm support and flexing assembly extending inwardly from a main cylindrical body of said lower housing, said diaphragm support and flexing assembly including a generally semi-circular projection extending therefrom on which the bottom surface of said flexible diaphragm is supported.

95. The resuscitation device of claim 94 and further including a filter retaining ring for securing the filter to the ventilation/exhalation valve member.

96. The resuscitation device of claim 95 wherein said filter retaining ring is secured to said lower housing.

* * * * *